US012371655B2

(12) United States Patent
Suntych

(10) Patent No.: US 12,371,655 B2
(45) Date of Patent: Jul. 29, 2025

(54) MULTI-MEDIA STRUCTURES CONTAINING GROWTH ENHANCEMENT ADDITIVES

(71) Applicant: Xiant Technologies, Inc., Greeley, CO (US)

(72) Inventor: Jon Daren Suntych, Greeley, CO (US)

(73) Assignee: Xiant Technologies, Inc., Greeley, CO (US)

( * ) Notice: Subject to any disclaimer, the term of this patent is extended or adjusted under 35 U.S.C. 154(b) by 285 days.

(21) Appl. No.: 18/196,795

(22) Filed: May 12, 2023

(65) Prior Publication Data

US 2023/0279343 A1 Sep. 7, 2023

Related U.S. Application Data

(63) Continuation-in-part of application No. 15/541,850, filed as application No. PCT/US2016/012690 on Jan. 8, 2016, now abandoned.

(60) Provisional application No. 62/101,845, filed on Jan. 9, 2015.

(51) Int. Cl.
*C12N 5/00* (2006.01)
(52) U.S. Cl.
CPC ........ *C12N 5/0025* (2013.01); *C12N 2500/02* (2013.01); *C12N 2500/34* (2013.01)
(58) Field of Classification Search
CPC .............. C12N 5/0025; C12N 2500/02; C12N 2500/34; A01G 24/00; A01G 24/40; A01G 24/44
USPC .......................................................... 47/59 S
See application file for complete search history.

(56) References Cited

U.S. PATENT DOCUMENTS

| 2,123,932 A | 7/1938 | Carriveau |
| 3,373,009 A | 3/1968 | Pruitt et al. |
| 3,734,987 A | 5/1973 | Hamrin et al. |
| 3,973,355 A | 8/1976 | McKenzie |
| 4,241,537 A | 12/1980 | Wood |
| 4,694,906 A | 9/1987 | Hutchins et al. |
| 4,808,430 A | 2/1989 | Kouno |
| 5,360,828 A | 11/1994 | Morrison |

(Continued)

FOREIGN PATENT DOCUMENTS

| CN | 101171272 A | 4/2008 |
| CN | 101503492 A | 8/2009 |

(Continued)

OTHER PUBLICATIONS

"Biotechnology of Horticultural Plant Textbook on Campus," Institute of Horticultural Biotechnology of South China Agricultural University, p. 115, 1st Edition.

(Continued)

*Primary Examiner* — Brady W Frazier
(74) *Attorney, Agent, or Firm* — Weatherly IP Solutions, LLC; James Weatherly; Karen Bechtold

(57) ABSTRACT

Embodiments described herein provide for multi-media structures 100 with growth enhancement additives for multiple stages of growth of an organism such as a plant, fungus or bacteria, including the production of individual media structures and multi-media structures 100 for multi-stage growth. Methods for the production of individual media structure and multi-media structures 100 with growth enhancement additives are provided. Methods for using multi-media structures 100 to grow an organism through multiple stages of growth such as root production, vegetative growth and flowering are also provided.

23 Claims, 13 Drawing Sheets

(56) References Cited

U.S. PATENT DOCUMENTS

| | | | |
|---|---|---|---|
| 5,543,321 | A | 8/1996 | Guri |
| 5,564,224 | A | 10/1996 | Carlson et al. |
| 5,870,854 | A | 2/1999 | Wilkins |
| 2005/0102895 | A1 | 5/2005 | Bissonnette et al. |
| 2007/0292643 | A1 | 12/2007 | Renn |
| 2008/0216404 | A1 | 9/2008 | Jarvis |
| 2009/0320367 | A1 | 12/2009 | Smith et al. |
| 2011/0041402 | A1 | 2/2011 | Teasdale |
| 2018/0000028 | A1 | 1/2018 | Suntych |

FOREIGN PATENT DOCUMENTS

| | | |
|---|---|---|
| CN | 107205349 B | 6/2021 |
| DE | 368423 | 3/1932 |
| DE | 1900488 A1 | 8/1970 |
| DE | 1958253 A1 | 5/1971 |
| DE | 19529221 A1 | 2/1996 |
| DE | 202005002795 U1 | 5/2005 |
| FR | 2196386 A1 | 3/1974 |
| GB | 889064 A | 2/1962 |
| GB | 1252206 A | 11/1971 |
| GB | 1279943 A | 6/1972 |
| JP | 62296842 A | 12/1987 |
| JP | 63137679 A | 6/1988 |
| JP | 63188389 A | 8/1988 |
| JP | 2257841 A | 10/1990 |
| JP | 2261373 A | 10/1990 |
| JP | 61166392 A | 7/1996 |
| JP | 10127805 A | 5/1998 |
| JP | 10155696 A | 6/1998 |
| JP | 1179860 A | 3/1999 |
| JP | 200467566 A | 3/2004 |
| JP | 200616501 A | 1/2006 |
| JP | 2006296354 A | 11/2006 |
| JP | 201468608 A | 4/2014 |
| JP | 2014198013 A | 10/2014 |
| WO | 2016112319 A1 | 7/2016 |

OTHER PUBLICATIONS

Advisory Action for U.S. Appl. No. 15/541,850 mailed Sep. 10, 2021.
Advisory Action for U.S. Appl. No. 15/541,850 mailed Sep. 15, 2022.
Amendment After Final Office Action for U.S. Appl. No. 15/641,850 submitted Aug. 15, 2022.
Amendment After Final Office Action for U.S. Appl. No. 16/541,850 submitted Aug. 24, 2021.
Amendment for U.S. Appl. No. 15/541,850 submitted Mar. 2, 2022.
Amendment for U.S. Appl. No. 15/541,850 submitted Mar. 8, 2021.
Amendment for U.S. Appl. No. 15/541,850 submitted May 12, 2023.
EP16735495, European Search Report, Jul. 31, 2018.
EP16735495, Response and amendment to claims, Feb. 14, 2019.
EP16735495, Response and amendment to claims, Feb. 7, 2020.
Final Office Action for U.S. Appl. No. 15/541,850 mailed Jun. 13, 2022.
Final Office Action for U.S. Appl. No. 15/541,850 mailed Jun. 21, 2023.
Final Office Action for U.S. Appl. No. 16/541,850 mailed Jun. 24, 2021.
First Office Action for Canadian Patent Application No. 2972485 dated Feb. 23, 2022, 5 pages.
Non-Final Office Action for U.S. Appl. No. 15/541,850 mailed Dec. 3, 2021.
Non-Final Office Action for U.S. Appl. No. 15/541,850 mailed Nov. 14, 2022.
Non-Final Office Action for U.S. Appl. No. 15/541,850 mailed Oct. 7, 2020.
Notification of Grant for Chinese Patent Application No. 201680005240.8 mailed Apr. 19, 2021 with English translation, 2 pages.
Office Action for counterpart EP Patent Application No. 16735495.0 mailed Aug. 12, 2019, 4 pages.
PCT/US16/12690, Search Report, May 31, 2016.
RCE and Amendment for U.S. Appl. No. 15/541,850 submitted Oct. 11, 2022.
RCE and Amendment for U.S. Appl. No. 15/541,850 submitted Oct. 22, 2021.
Response to First Office Action for Canadian Patent Application No. 2972485 dated Jun. 23, 2022, 27 pages.
Response to Restriction Requirement for U.S. Appl. No. 15/541,850 submitted May 26, 2020.
Response to Second Office Action for Canadian Patent Application No. 2972485 dated May 17, 2023, 22 pages.
Response to Second Office Action for Chinese Patent Application No. 201680005240.8 with English translation of amended claims submitted Sep. 14, 2020, 25 pages.
Restriction Requirement for U.S. Appl. No. 15/541,850 mailed Apr. 16, 2020.
Second Office Action for Canadian Patent Application No. 2972485 dated Jan. 18, 2023, 4 pages.
Second Office Action for Chinese Patent Application No. 201680005240.8 with English translation dated Jun. 29, 2020, 25 pages.

Top perspective view of the arrangement of media in the multi-media structure shown in Figures 1 and 2

300

Example apparatus for infusing gas into a gelatinous solution
400

409 gelatinous solution
container 401
porous material 403
405 tubing
407 air compressor Gas infused gelatinous compound after solidification and removal from container having uniform gas bubbles
411

Example of stacked gelatinous compounds having different densities and infused with gas
800

MULTI-MEDIA STRUCTURES CONTAINING GROWTH ENHANCEMENT ADDITIVES

CROSS REFERENCE TO RELATED APPLICATION

The present application is a continuation in part of and claims priority to U.S. application Ser. No. 15/541,850, as filed Jul. 6, 2017, which was a national phase application that claims priority to Patent Cooperation Treaty Application No. PCT/US2016/012690, as filed Jan. 8, 2016, which claims priority to U.S. Application No. 62/101,845, as filed on Jan. 9, 2015, entitled "Gas Infused Gelatinous Compounds", the entire contents of both applications are incorporated herein by reference for all purposes.

BACKGROUND

A variety of methods are used for growing organisms in a controlled environment. An example conventional method uses a shallow tray or pot with seed-growing potting soil, and often times the seeds are covered by glass, newspaper, or plastic to retain moisture. Another example, hydroponic systems, is a soil-less method wherein the plant roots are immersed in water containing plant food. The plants are held in place and upright by some type of granular material.

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

SUMMARY

The following embodiments and aspects thereof are described and illustrated in conjunction with systems, tools and methods, which are meant to be exemplary and illustrative, not limiting in scope.

An embodiment of the present disclosure provides a multi-media gelatinous structure for the growth of an organism, wherein said structure comprises: a first gelatinous compound, wherein said first gelatinous compound comprises at least one growth enhancement additive selected from gas, hormones, essential oils, antimicrobial agents, herbicides, pesticides, and microbes; a second gelatinous compound, wherein said second gelatinous compound is infused with a gas and comprises at least one growth enhancement additive selected from hormones, essential oils, antimicrobial agents, herbicides, pesticides, and microbes, and wherein the at least one growth enhancement additive of the second gelatinous compound is different from or in a different quantity from the at least one growth enhancement additive of the first gelatinous compound; wherein said first gelatinous compound and said second gelatinous compound are produced by a combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch; wherein the density of said gelatinous compound of said first gelatinous compound is greater than the density of said gelatinous compound of said second gelatinous compound; and wherein said first gelatinous compound is embedded within said second gelatinous compound to create a multi-media gelatinous structure.

An embodiment of the present disclosure provides a method for growing plants in a multi-media gelatinous structure, wherein said method comprises: dissolving a gelling agent, wherein said gelling agent consists of any one or any combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch; and one or more growth enhancement additives into a first aqueous solution, wherein said one or more growth enhancement additives are selected from gas, hormones, essential oils, antimicrobial agents, herbicides, pesticides, and microbes and dissolving a gelling agent, wherein said gelling agent consists of any one or any combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch, and one or more growth enhancement additives into at least one second aqueous solution, wherein said one or more growth enhancement additives are selected from gas, hormones, essential oils, antimicrobial agents, herbicides, pesticides, and microbes; pouring said first aqueous solution and said at least one second aqueous solution into separate containers; allowing said first aqueous solution and said at least one second aqueous solution to solidify to produce a first gelatinous compound and a second gelatinous compound, wherein the density of said first gelatinous compound is greater than the density of said second gelatinous compound; releasing said gelatinous compounds from said containers; embedding said first gelatinous compound within said second gelatinous compound to create a stacked gelatinous media; placing a plant on the surface of said first gelatinous compound of said stacked gelatinous media; and growing said plant in said stacked gelatinous media.

An embodiment of the present disclosure provides a method for growing an organism through multiple stages of growth, the method comprising: providing a multi-media structure comprising at least a first gelatinous compound and a second gelatinous compound, wherein the first gelatinous compound comprises at least one growth enhancement additive is selected from gas, hormones, essential oils, antimicrobial agents, herbicides, pesticides, and microbes; and wherein said second gelatinous compound comprises at least one growth enhancement additive is selected from gas, hormones, essential oils, antimicrobial agents, herbicides, pesticides, and microbes; and wherein the at least one growth enhancement additive of the second gelatinous compound is different from or in a different quantity from the at least one growth enhancement additive of the first gelatinous compound; and wherein said first gelatinous compound and said second gelatinous compound are produced by a combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch, wherein the density of said gelatinous compound of said first gelatinous compound is greater than the density of said gelatinous compound of said second gelatinous compound; providing an organism and establishing said organism on the surface of said first gelatinous compound, wherein said organism is established on said first gelatinous compound; growing said organism on said first gelatinous compound; allowing said organism to grow through said first gelatinous compound and into said second gelatinous compound.

An embodiment of the present disclosure comprises a method for growing an organism through multiple stages of growth, the method comprising: providing a multi-media structure comprising at least two media, wherein the first media comprises at least one growth enhancement additive; providing an organism and establishing said organism on said first media; growing an organism in said first media, wherein said first media induces a first stage of growth; a second media, wherein said second media comprises at least one growth enhancement additive, and wherein the at least one growth enhancement additive of the second media is different from the at least one growth enhancement additive of the first media; growing an organism from first media into said second media, wherein said second media induces a second stage of growth in said organism.

An embodiment of the present disclosure further comprises a method for growing one or more organisms in a multi-media structure comprising at least two media: providing a first media, where the first media comprises at least one growth enhancement additive; providing a second media, where the second media comprises at least one growth enhancement additive, and where the at least one growth enhancement additive of the second media is different from the at least one growth enhancement additive of the first media; embedding the first media within the second media; and growing an organism in the multi-media structure comprising two media.

An embodiment of the present disclosure further comprises a multi-media structure for the growth of an organism, where the structure comprises: at least one first media, wherein the first media comprises at least one growth enhancement additive; at least one second media, where the second media comprises at least one growth enhancement additive, and where the at least one growth enhancement additive of the second media is different from the at least one growth enhancement additive of the first media; and wherein said first media is embedded within said second media.

An embodiment of the present disclosure provides a system for producing a gas infused gelatinous compound, where the system comprises: a container; a porous material, where the container is operably coupled to the porous material; a means for forcing gas into the container through the porous material; and a conduit; where the conduit is operably coupled to the porous material and the means for forcing gas, and a gelling agent in an aqueous solution, where the solution is poured into the container.

An embodiment of the present disclosure further comprises a method for growing one or more organisms in a stacked gelatinous compound, wherein said method comprises dissolving a gelling agent in two or more aqueous solutions to produce gelatinous solutions of different densities; wherein each gelatinous solution contains one or more growth enhancement additives; pouring said gelatinous solutions having different densities into containers; allowing each gelatinous solution to solidify to produce gelatinous compounds of different densities, stacking said gelatinous compounds having different densities, and growing an organism in said stacked gelatinous compounds.

In addition to the example, aspects and embodiments described above, further aspects and embodiments will become apparent by reference to the drawings and by study of the following descriptions, any one or all of which are within the embodiments of the invention. The summary above is a list of example implementations, not a limiting statement of the scope of the embodiments of the invention.

BRIEF DESCRIPTION OF THE FIGURES

The accompanying drawings, which are incorporated herein and form a part of the specification, illustrate some, but not the only or exclusive, example embodiments and/or features. It is intended that the embodiments and figures disclosed herein are to be considered illustrative rather than limiting.

DETAILED DESCRIPTION

An embodiment of the present disclosure comprises systems and methods for producing a multi-media structure, where at least two media are provided, where each media is made up of a different composition, including growth enhancement additives. The first media is then embedded within the second media. These growth enhancement properties may include but are not limited to, infusion of one or more gases, hormones, nutrients, surfactants, antimicrobial agents, essential oils, herbicides, pesticides, and any combinations thereof, depending on the organism that is to be grown and the type of growth desired.

As will be discussed in further detail below, the multi-media structure of the present disclosure allows an organism, such as a plant, fungus or bacteria, to grow through multiple growth stages such as rooting or initial hyphae production, vegetative growth or hyphal production, flowering, fruiting body production, fruit and seed production. Each media of the multi-media structure is designed to encourage a specific type of growth.

Figure 1:
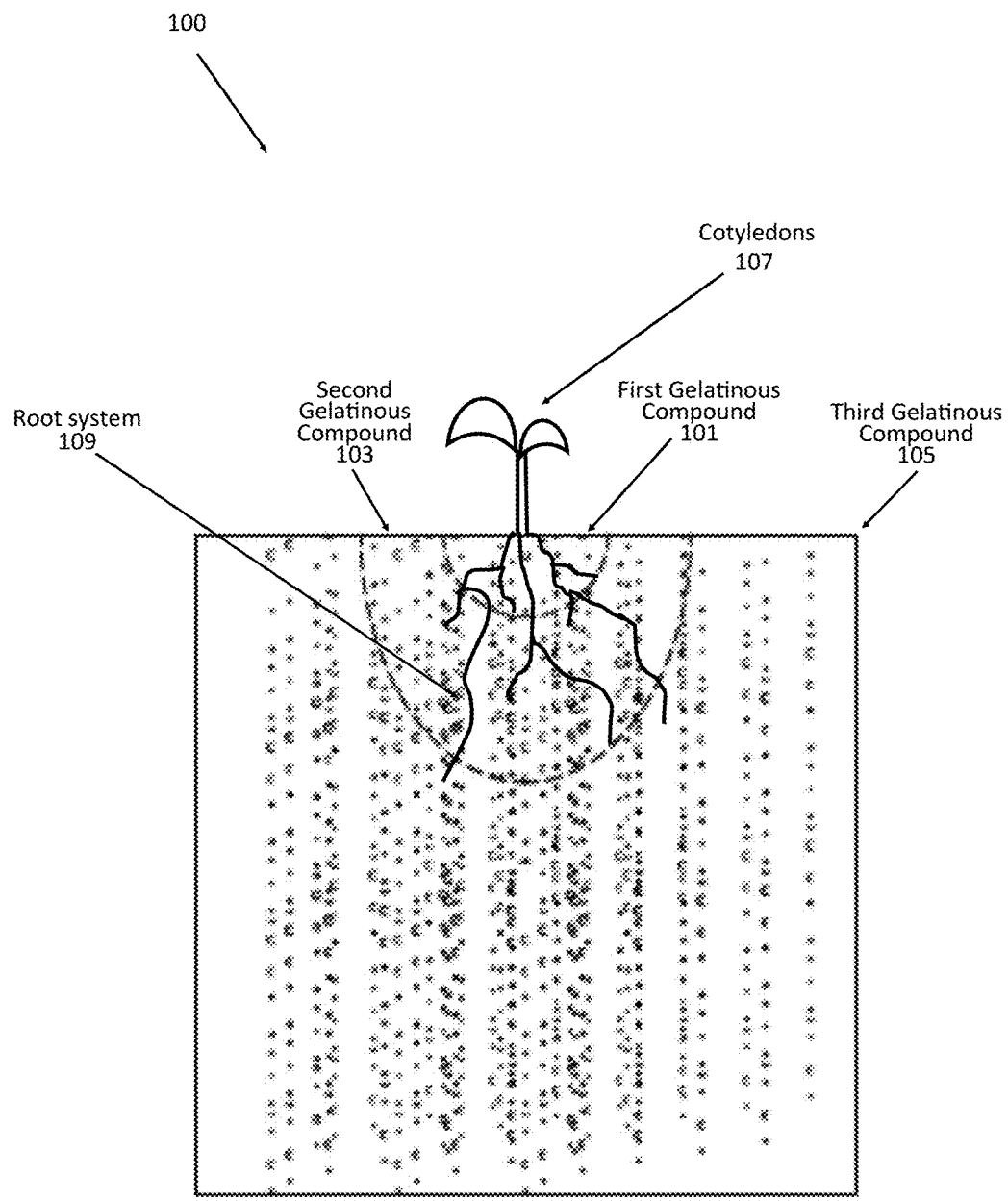
FIG. 1 shows an example of an organism, such as a plant, grown on a multi-media structure comprised of three different gelatinous compounds embedded within each other.

FIG. 1 provides an example of an organism, such as a plant, grown on a multi-media structure comprised of three different gelatinous compounds embedded within each other 100. In the multi-media structure 100 of FIG. 1, a first gelatinous compound 101 is provided, where the first gelatinous compound 101 contains one or more growth enhancement additives and wherein the first gelatinous compound 101 has a density. The first gelatinous compound 101 is formed by taking a gelling agent, such as agar or pectin, which is dissolved in an aqueous solution to produce a liquid gelatinous solution. One or more growth enhancement additives, such as a gas, hormones, nutrients, surfactants, antimicrobial agents, essential oils, herbicides, pesticides, and any combinations thereof are then added to the liquid gelatinous solution. The gelatinous solution is allowed to solidify.

A second gelatinous compound 103 is provided in FIG. 1, where the second gelatinous compound 103 contains one or more growth enhancement additives, which may be different from or in different quantities from the additives of the first gelatinous compound 101. As with the first gelatinous compound, 101, the second gelatinous compound 103 is also formed by taking a gelling agent, such as agar or pectin, which is dissolved in an aqueous solution to produce a liquid gelatinous solution, more or less gelling agents solutions may also be added to increase or decrease the density of the solution, where the density of the second gelatinous compound 103 is different from the first gelatinous compound 101. One or more growth enhancement additives, such as a gas, hormones, nutrients, surfactants, antimicrobial agents, essential oils, herbicides, pesticides, and any combinations thereof are then added to the liquid gelatinous solution. The gelatinous solution is allowed to solidify.

A third gelatinous compound 105 is provided in FIG. 1, where the third gelatinous compound 105 contains one or more growth enhancement additives, which may be different from or in different quantities from the additives of the first gelatinous compound 101 and the second gelatinous compound 103. As with the first gelatinous compound, 101 and the second gelatinous compound 103, the third gelatinous compound 105 is also formed by taking a gelling agent, such as agar or pectin, which is dissolved in an aqueous solution to produce a liquid gelatinous solution, more or less gelling agents solutions may also be added to increase or decrease the density of the solution. One or more growth enhancement additives, such as a gas, hormones, nutrients, surfactants, antimicrobial agents, essential oils, herbicides, pesticides, and any combinations thereof are then added to the liquid gelatinous solution. The gelatinous solution is allowed to solidify.

As further shown in FIG. 1, the first gelatinous compound 101 is embedded into the second gelatinous compound 103, exposing at least a portion of the surface of the first gelatinous compound 101 to the environment. The first gelatinous compound 101 has a shape that substantially corresponds to the shape of a well formed or carved in the second gelatinous compound 103. The second gelatinous compound 103 is embedded into the third gelatinous compound 105, exposing at least a portion of the surface of the second gelatinous compound 103 to the environment. The second gelatinous compound 103 has a shape that substantially corresponds to the shape of the well formed or carved in the third gelatinous compound 105.

In an example embodiment, the first gelatinous compound 101 is embedded into the second gelatinous compound 103, where the first gelatinous compound 101 has a density that is greater than the density of the second gelatinous compound 103, and exposing at least a portion of the surface of the first gelatinous compound 101 to the environment. The first gelatinous compound 101 has a shape that substantially corresponds to the shape of a well formed or carved in the second gelatinous compound 103. The second gelatinous compound 103 is embedded into the third gelatinous compound 105, where the second gelatinous compound 103 has a density that is greater than the density of the third gelatinous compound 105, and exposing at least a portion of the surface of the second gelatinous compound 103 to the environment. The second gelatinous compound 103 has a shape that substantially corresponds to the shape of the well formed or carved in the third gelatinous compound 105.

By having the density of each gelatinous compound decrease with each compound moving from the center of the gelatinous structure, increases the structure and support for young plant roots, allowing for that support and structure to decrease as the plant matures.

As further shown in FIG. 1, a dicot plant 107 is provided with a root system 109 growing through the three gelatinous compounds 101, 103, and 105. In an example embodiment of the current disclosure, each gelatinous compound has a specific growth additive for a specific stage of growth for the plant. For example, in the first gelatinous compound 101, a root-inducing compound or rooting hormone is incorporated into the compound. A seed, plant tissue culture or unrooted cutting is placed on the exterior surface of the first compound or under the exterior surface of the compound. The rooting hormone initiates root production of the plant 107. As the roots 109 continue to develop, they grow through the first gelatinous compound 101 and into the second gelatinous compound 103, the roots 109 encounter compounds that stimulate vegetative growth of the plant 107, such as plant hormones or plant growth regulators. This encourages vegetative growth of the plant 107 and continued root 109 development. As the roots 109 continue to develop, they growth through the second compound 103 and into the third compound 105. Here the roots 109 may encounter compounds within the third gelatinous compound 105 that induce flowering, such as gibberellic acid or ethephon.

In another embodiment, as further shown in FIG. 1, a dicot plant 107 is provided with a root system 109 growing through the three gelatinous compounds 101, 103, and 105. In an example embodiment of the current disclosure, the density of each gelatinous compound decreases from the first compound to the second to the third for a specific stage of growth for the plant. That is density of the first compound is greater than the density of the second compound with the density of the second compound great than the density of the third compound.

In another embodiment, as further shown in FIG. 1, a dicot plant 107 is provided with a root system 109 growing through the three gelatinous compounds 101, 103, and 105. In an example embodiment of the current disclosure, the density of each gelatinous compound increases from the first compound to the second to the third for a specific stage of growth for the plant. That is density of the first compound is less than the density of the second compound with the density of the second compound less than the density of the third compound.

For example, in the first gelatinous compound 101, a root-inducing compound or rooting hormone is incorporated into the compound. A seed, plant tissue culture or unrooted cutting is placed on the exterior surface of the first compound or under the exterior surface of the compound. The rooting hormone initiates root production of the plant 107. As the roots 109 continue to develop, they grow through the first gelatinous compound 101 and into the second gelatinous compound 103, the roots 109 encounter compounds that stimulate vegetative growth of the plant 107, such as plant hormones or plant growth regulators. This encourages vegetative growth of the plant 107 and continued root 109 development. As the roots 109 continue to develop, they growth through the second compound 103 and into the third compound 105. Here the roots 109 may encounter compounds within the third gelatinous compound 105 that induce flowering, such as gibberellic acid or ethephon.

Figure 2:
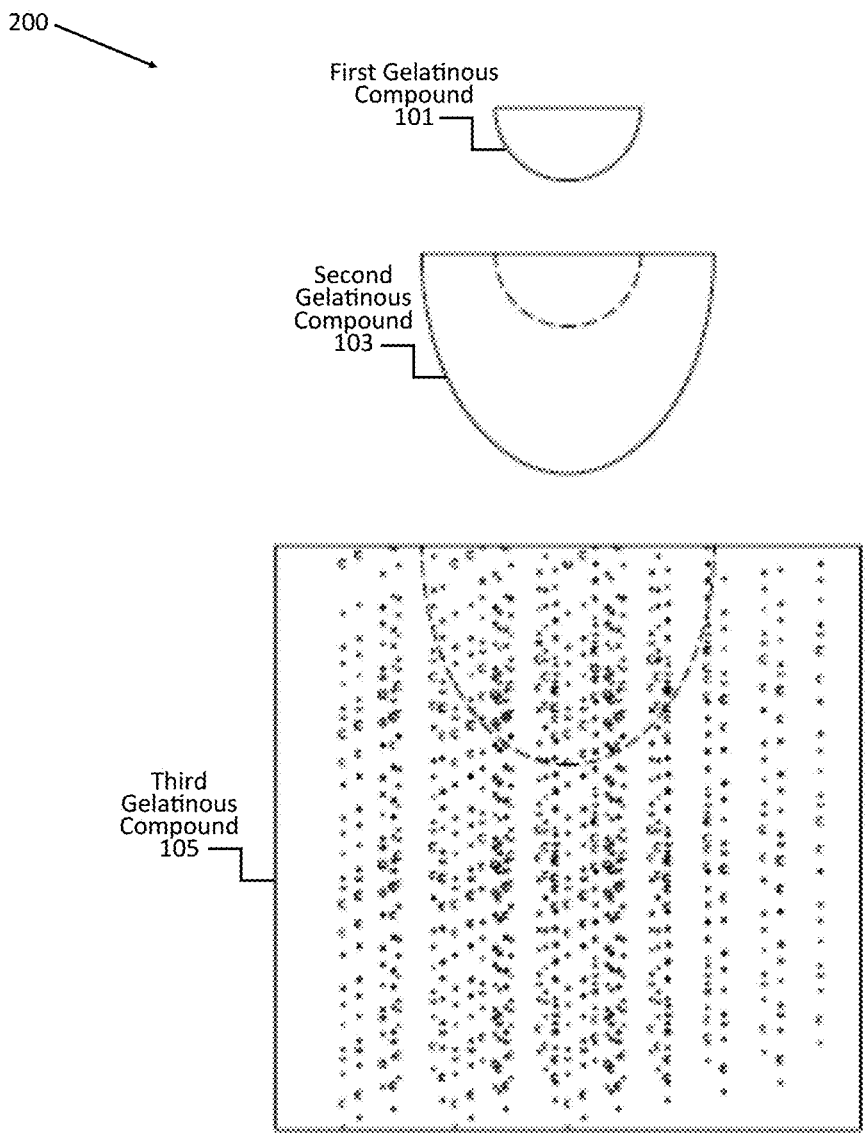
FIG. 2 shows a side view of the media components of the multi-media structure shown in FIG. 1.

FIG. 2 shows a side view of the different components of the multi-media structure shown in FIG. 1. While a bowl or well-shaped cavity is shown in FIGS. 1 and 2 for the embedding of the gelatinous compounds 101, 103, and 105, any shape may be used to fit the media together, including but not limited to, square, rectangle, triangle, oval, trapezium, diamond, rhombus, parallelogram, pentagon, hexagon, heptagon, and octagon.

Figure 3:
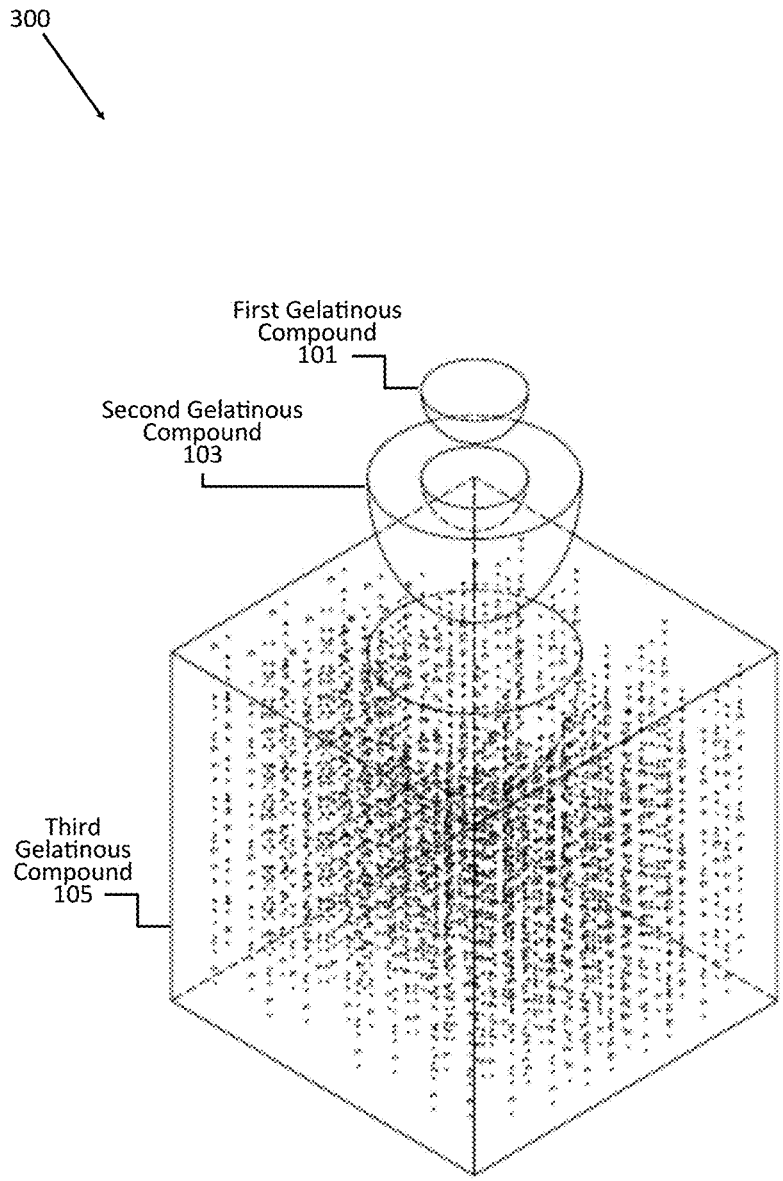
FIG. 3 shows a top perspective view of the arrangement of media in the multi-media structure shown in FIGS. 1 and 2.

FIG. 3 shows a top perspective view of the arrangement of media in the multi-media structure shown in FIGS. 1 and 2. As shown in FIG. 3, the first gelatinous compound 101 fits within the second gelatinous compound 103. The second gelatinous compound 105 fits within the third gelatinous compound.

A variety of sizes may be used for the multi-media structure shown in FIGS. 1-3. For example, the volume of the first gelatinous compound may be 0.1% to 99% of the volume of the second gelatinous compound. Similarly, the second gelatinous compound may be 0.1% to 99% of the volume of the third gelatinous compound, and so forth.

In the example multi-media structure shown in FIGS. 1, 2, and 3, three gelatinous compounds 101, 103, and 105 are illustrated but any number of gelatinous compounds can be used. Therefore, while this descriptive example has a multi-media structure with three gelatinous compounds 101, 103, and 105, it should be understood that this description is applicable to any such multi-media structure with other numbers of gelatinous compounds, as will be understood by one skilled in the art, once they understand the principles of this invention.

While a dicotyledonous plant 107 is shown in FIG. 1, the multi-media structure 100 may also be used for monocots and dicots (Angiosperms), Gymnosperms, Pteridophytes, Bacteria, and Fungi. While variations of gelatinous compounds are shown in FIGS. 1-3, the media may include, for example, non-aerated agar, soil, peat and peat-like materials, straw, hay, wood residues, sugar cane bagasse, rice hulls, sand, perlite, vermiculite, calcined clays, expanded polystyrene, and urea formaldehydes. The media may be transparent or semi-transparent to allow light to penetrate.

As used herein, a gelling agent may consist of any one or any combination of hydrocolloids, including but not limited to, pectin, gelatin, agar-agar ("agar"), such as malt extract agar (MEA), potato dextrose agar (PDA), yeast extract agar (YEA), xanthan gum, guar gum, locust bean gum, gum arabic, carrageenan, silica gel, cellulose and cellulose derivatives such as carboxymethyl cellulose, alginate, and starch. Any number of densities may be achieved depending on the percentage of gelling agent to aqueous solution used. Solvation may be achieved by heating the gelling agent and aqueous solution.

Various additives may be added to the gelatinous compound to enhance the growth of one or more organisms.

Additive Examples

A. Gas

An example of a growth enhancement additive that may be added to one or more media of the multi-media structures may include the infusion or aeration of gas into the media, including but not limited to oxygen, carbon dioxide, ethylene, nitrogen, argon, methane, helium, and combinations thereof, as well as the length of aeration time.

Aeration or infusion of gas would occur while the gelatinous solution is still warm, and once the desired composition is achieved, the gelatinous compound is allowed to cool and solidify. Aeration of the gelatinous solution may be achieved by forcing gas into the gelatinous material such as through a porous material, such as soapstone or a similar material, a vacuum process, a foam gun, foam sprayer or various chemical agents, such as the infusion of solutions using hydrogen peroxide and yeast, as well as chemical reactions, including foaming agents may be used.

An example of the aeration of the gelatinous solution 2 teaspoons of yeast is added to the gelatinous solution and mixed together then a ½ cup of 3% to 6% hydrogen peroxide is added to the gelatinous solution. The reaction aerates the solution, while the solution cools.

Figure 4A:
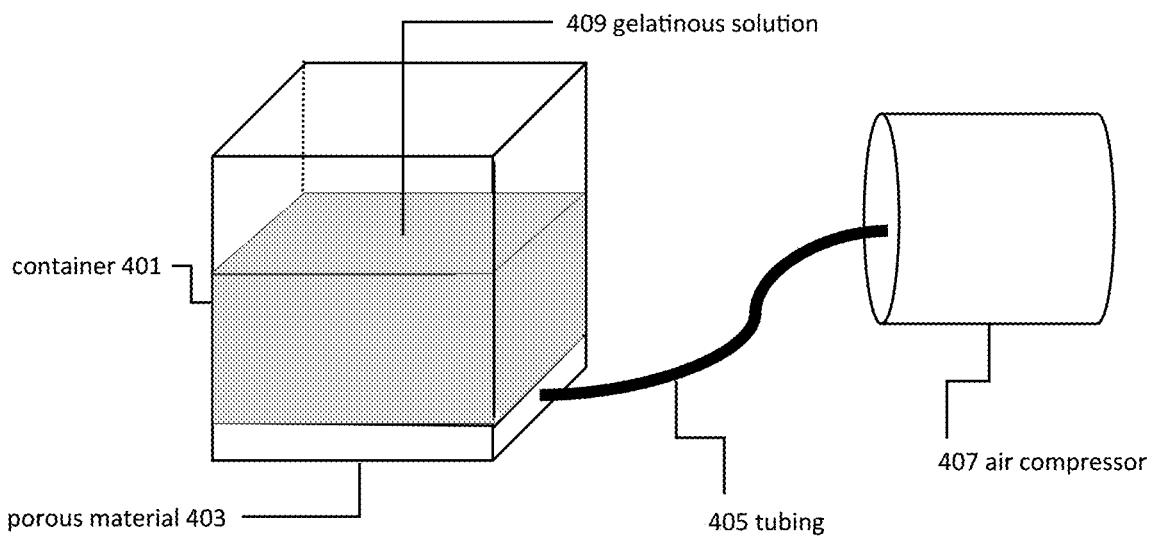
FIG. 4A is an illustration of an example apparatus for infusing gas into a gelatinous solution.

An example apparatus for infusing gas into a gelatinous solution or compound is shown in FIG. 4A. As shown in FIG. 4A, a container 401 is provided having a porous material 403. A gelatinous solution 409 is poured into the container, where the base of the container made of the porous material supports the gelatinous solution 409. A means for forcing air or gas through the porous material and into the container is provided, such as a hand pump, foot pump, gas cylinder, or a gas compressor 407. The means for forcing air or gas 407 is operably connected to the porous material 403 through a conduit such as tubing 405. Gas is forced through the tubing 405 and porous material 403 and infiltrates the gelatinous solution 409 producing bubbles.

Figure 4B:
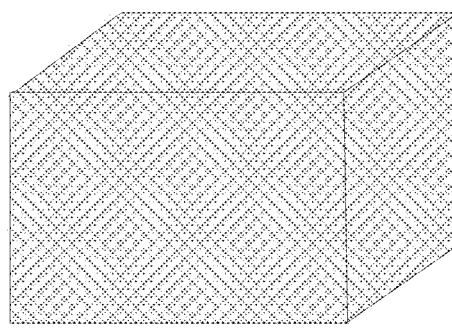
FIG. 4B is an illustration of a gas infused gelatinous compound after solidification and removal from container

The composition of gas to gelatinous solution as well as the size and uniformity of gas bubbles may be customized by the porous material used, the aeration method, such as the use of a foam gun, vacuum or chemical agents, such as the infusion of solutions using hydrogen peroxide and yeast, as well as chemical reactions, the type of gas, including but not limited to oxygen, carbon dioxide, ethylene, nitrogen, argon, methane, helium, and combinations thereof, as well as the length of aeration time. An example of a gas infused gelatinous compound after solidification and removal from container having uniform gas bubbles 411 throughout is shown in FIG. 4B. Gas compressors, such as the one shown in FIG. 4A, may come with multi-outlet diverter, so that multiple gelatinous solutions may be infused with a gas at the same time.

Figure 5:
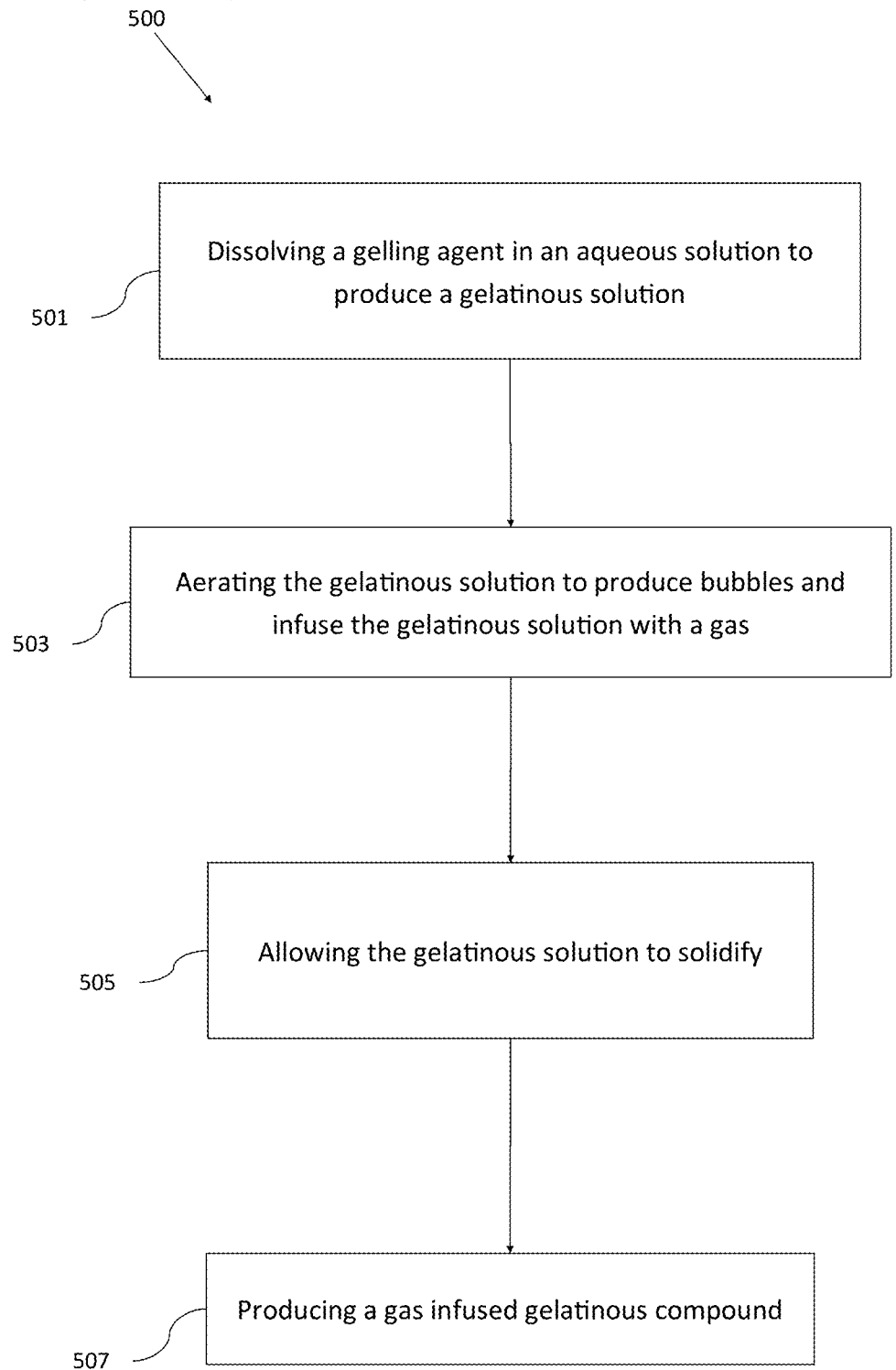
FIG. 5 is a flow diagram for producing a gas infused gelatinous compound.

FIG. 5 provides a flow diagram showing the steps for producing a gas infused gelatinous compound, 500. As shown in FIG. 5, in step 501, a gelling agent, such as agar or pectin, is dissolved in an aqueous solution to produce a gelatinous solution. In step 503, the gelatinous solution is aerated to produce bubbles and infuse the gelatinous solution with a gas. In step 505, the gelatinous solution is allowed to solidify. In step 507 a gas infused gelatinous compound is produced.

The gas infused gelatinous compounds may be formed in any size or shape, as the gelatinous solution may be poured into a container or mold prior to the gel setting. For example, the gas infused gelatinous compound may be poured into a petri dish, a jar, a plant container, or a multi-chambered container. The gas infused gelatinous compound may be spread very thinly, or may be very thick, and may be released from the mold after solidifying or the gelatinous compounds may remain in the container.

The gas infused gelatinous compounds, described here may be transparent or semi-transparent, and support the growth of an organism such as algae, fungi, bacteria or a plant. The use of the transparent or semi-transparent agar may increase tissue growth, tissue quality and health; an example may be seen in plants where light through the transparent agar may stimulate meristematic tissue growth and/or root growth. Microorganisms such as algae, fungi or bacteria may be streaked out on the surface of the gelatinous compound of a multi-media structure, spread evenly, or dispersed throughout via the pour plate technique. Plants may be started from seed, tissue culture, rhizome, or vegetative cuttings such as unrooted cuttings. Due to the support and structure provided by the agar, organisms may be grown vertically or inverted, depending on the need and the desired growth.

Figure 6:
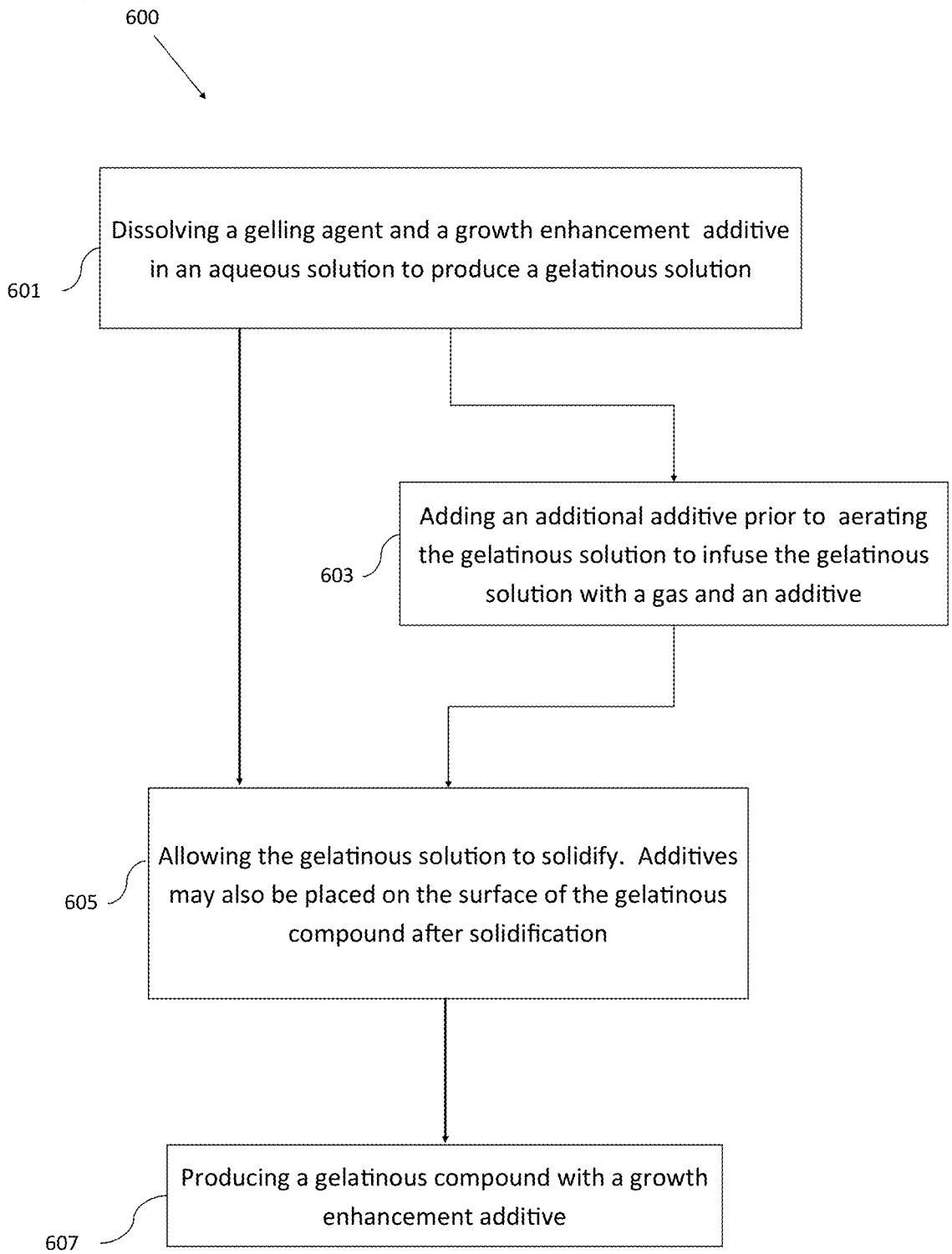
FIG. 6 is a flow diagram for producing a gelatinous compound with an additive.

Additional additives may be added with or without aeration of the gelatinous compound. FIG. 6 provides a flow diagram for producing a gelatinous compound with an additive 600. In step 601, growth enhancement additives may be dissolved with the gelling agent in an aqueous solution. If solvation of the gelling agent is achieved by heating, and the desired growth enhancement additive is sensitive to heat, the additive may be added prior to aeration 603, when the solution has cooled but not solidified. In step 605, growth enhancement additives may be added to the surface of the gelatinous compound after solidification. In step, 607 a gelatinous compound is produced with a growth enhancement additive 607.

B. Hormones

Rooting hormones, tip growth hormones, and plant growth hormones may be incorporated into various layers of the gelatinous compound. One or more rooting compound or hormones, such as willow extract or honey may be added to the gelatinous solution to induce rooting of unrooted cuttings.

C. Surfactants

Aeration of gelatinous solutions, such as those containing cellulose or cellulose derivatives may be enhanced through the addition of a surfactant. Surfactants may also be used to increase foaming.

D. Nutrients

Such nutrients may include, but are not limited to, organic and inorganic compounds, hormones, amino acids, peptides and proteins, growth factors such as extracts of beef, brain, heart, and yeast, blood and serum as would be required by fastidious microbes, salts and minerals such as calcium, phosphorus, magnesium, sodium, potassium, chloride, sulfur, manganese, iodine, cobalt, fluoride, selenium, iron, copper, and zinc, alcohol, carbohydrates, and sugars such as glucose, sucrose, lactose, mannitol, inositol, and arabinose, fatty acids, vitamins, ions, and microorganisms, such as rhizobium, ectomycorrhizal fungi or endomycorrhizal fungi.

E. Antimicrobial Agents

Antimicrobial agents may be added to the gelatinous compound may include, for example, antibiotics and antifungals.

F. Essential Oils

Essential oils may be added to the gelatinous compound to inhibit microbial growth are well known in the art, and may include, but are not limited to, camphor oil, citronella oil, *Origanum vulgare* L. essential oil, *Origanum majorana* L. essential oil, lemongrass oil, ajowan oil, dill oil, geranium Egyptian oil, rosemary oil, tea tree oil, thyme oil, cumin oil, the essential oils of *Cassulia allaris* and *Mentha arvensis*, cinnamon oil, and palmarosa oil.

G. Herbicides

Herbicides may be added to the gelatinous compound to prevent the growth of specific plant and may include but are not limited to glyphosate, glufosinate, bromoxynil, L-phosphinothricin, triazine, PPO-inhibitors, methyl viologen, sulfonylurea, immidazolinone, dicamba, phenoxy propionic acid, cyclohexone, cyclohexanedione, and benzonitrile.

H. Pesticides

Pesticides may be added to the gelatinous compound for controlling or preventing the growth of unwanted organisms, such as insecticides and acaracides, biorationals (biorational pesticides or biopesticides), pyrethroids, pyrethrum, carbamates, and organophosphates.

I. Microbial Enhancement

Microbes may be added to the gelatinous compound to increase nutrient uptake depending on the organism and may include various forms of rhizobium and mycorrhizae.

J. Growth Substrates

Substrates may be added to the gelatinous compound or may encapsulate a layer of gelatinous material in various quantities depending on the organism and types of growth desired. Examples of substrates that may be added to the gelatinous materials may include but are not limited to: straw, hay, rye, oak, saw dust, sugarcane bagasse, peat, vermiculite, and rice flower cakes.

As used herein "organism" includes an assembly of molecules functioning as a more or less stable whole that exhibits the properties of life. As will be discussed further, organisms may include but are not limited to unicells and multicellular life forms, viruses, animals (including but not limited to vertebrates (birds, mammals, amphibians, reptiles, fish); mollusks (clams, oysters, octopuses, squid, snails); arthropods (millipedes, centipedes, insects, spiders, scorpions, crabs, lobsters, shrimp); annelids (earthworms, leeches); sponges; and jellyfish), microorganisms, algae, bacteria, fungi, gymnosperms, angiosperms and pteridophytes, cyanobacteria or eukaryotic green algae.

As used herein, the term "plant" includes plant cells, plant protoplasts, plant cell tissue cultures from which plants can be regenerated, plant calli, plant clumps, and plant cells that are intact in plants or parts of plants, such as embryos, pollen, ovules, flowers, pods, leaves, roots, root tips, anthers, cotyledons, hypocotyls, meristematic cells, stems, pistils, petiole, and the like.

As used herein, the term "tissue culture" indicates a composition comprising isolated cells of the same or a different type or a collection of such cells organized into parts of an organism, such as a plant. Exemplary types of plant tissue cultures are protoplasts, calli, plant clumps, and plant cells that can generate tissue culture that are intact in plants or parts of plants, such as embryos, pollen, flowers, seeds, pods, petioles, leaves, stems, roots, root tips, anthers, pistils, and the like. Means for preparing and maintaining plant tissue culture are well known in the art.

The gelatinous compound of the present disclosure can replace other types of plant media, such as soil, peat and peat-like materials, wood residues, sugar cane bagasse, rice hulls, sand, perlite, vermiculite, calcined clays, expanded polystyrene, and urea formaldehydes. The gelatinous compound of the present disclosure is lightweight, and yields improved plant growth due to the growth enhancement additives of the media. Further, if a reversible hydrocolloid is used as the gelling agent, one can release the plant from the gelatinous compound by heating and gentle agitation of the agar. Once released from the gelatinous compound the plant may be transplanted to a different plant medium.

Figure 7:
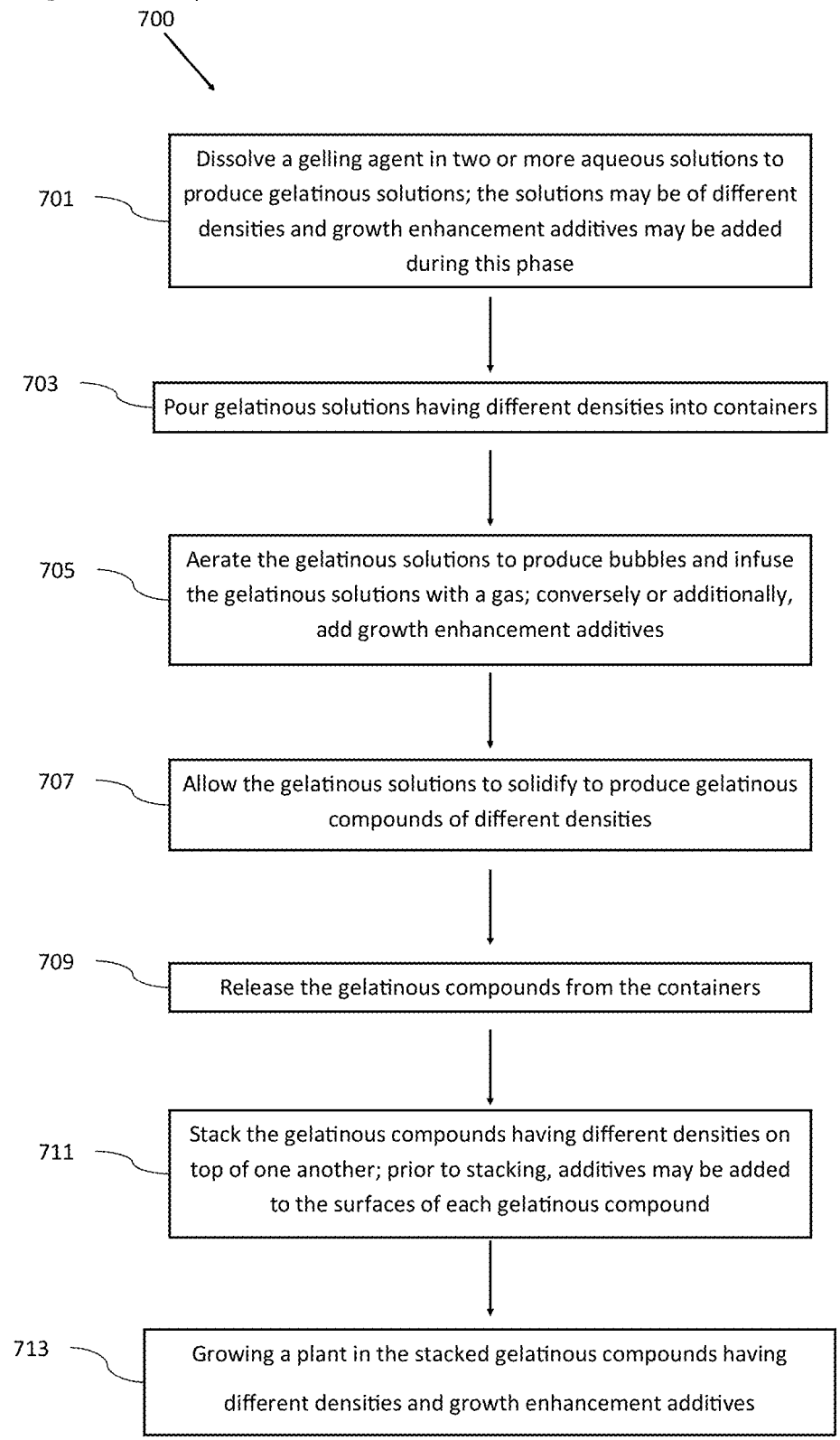
FIG. 7 is a flow diagram for growing plants in stacked gelatinous compounds.

Shown in FIG. 7 is a flow diagram for growing plants in stacked gas infused gelatinous compounds 700. In step 701, a gelling agent is dissolved in two or more aqueous solutions to produce gelatinous solutions of different densities. Growth enhancement additives may be also be dissolved in the aqueous solution at this time. This step 703, the gelatinous solution is poured into containers. In step 705, the gelatinous solutions may be aerated to produce bubbles or gas pockets within the gelatinous solution, infusing the gelatinous solutions with a gas, or may have other growth enhancement additives added. In step 707, the gelatinous solutions are allowed to solidify to produce gelatinous compounds of different densities. In step 709, the gelatinous solution, now in a solid state, may be released from the containers or the gelatinous compounds may remain in the container. In step 711, the gelatinous compounds having different densities are then stacked on top of one another to create a multi-media structure. Prior to stacking, growth enhancement additives may be placed on the surface of one or more of the gelatinous compounds. In step 713, a plant is grown on a multimedia structure having stacked gelatinous compounds. The varying densities and growth enhancement additives can be customized towards a specific organism to support multiple phases of growth.

Figure 8A:
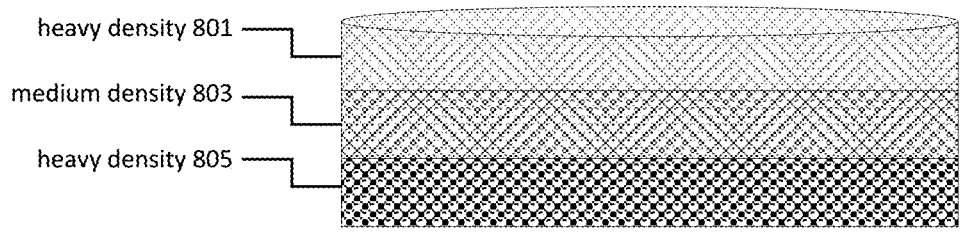
FIG. 8A shows an example of a stacked gelatinous compound having varying densities and infused with gas.
Figure 8B:
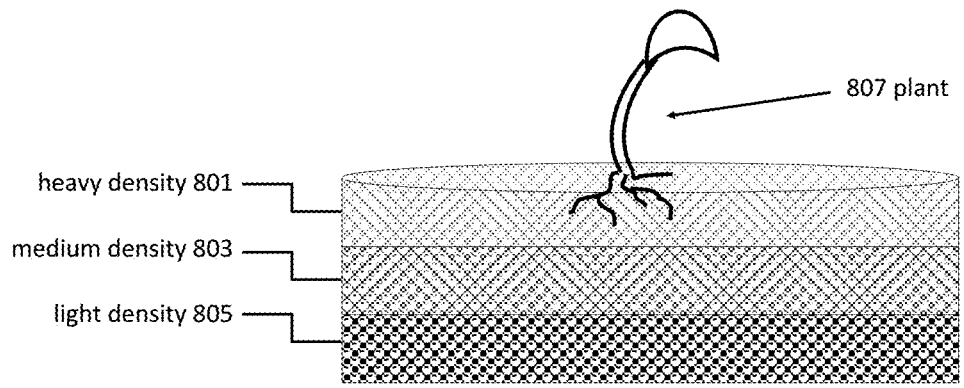
FIG. 8B shows a plant growing in stacked gelatinous compounds.
Figure 8C:
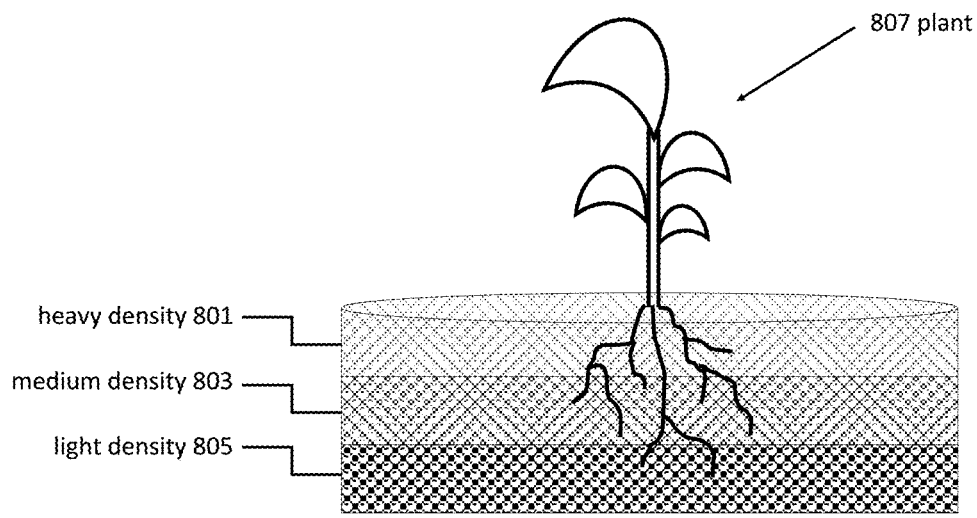
FIG. 8C shows a plant growing in stacked gelatinous compounds.

An example of a multimedia structure with stacked gelatinous compounds of varying densities is shown in FIG. 8A, FIG. 8B, and FIG. 8C. The gelatinous compound of the multimedia structure having different densities and different additives allows for varying amounts of support of the plant, in this example, so that all phases of growth are supported while encouraging different phases of growth. In the example shown in FIGS. 8A, 8B and 8C, a gelatinous compound having a heavy density 801 is stacked on top of another gas infused gelatinous compound having a medium density 803, which is stacked on top of another gas infused gelatinous compound having a light density 805. In the example shown in FIG. 8B, a plants root system grows first through the gas infused gelatinous compound of heaviest density 801, and then proceeds through to the agar, providing the highest amount of structure and support to the organism (FIG. 8C). In the example shown in FIGS. 8A, 8B, and 8C, all growth phases of the plant are supported, from seed, to seedling, to a mature plant. The stacked gelatinous compound may be transparent or semi-transparent to allow light to penetrate.

Figure 9:
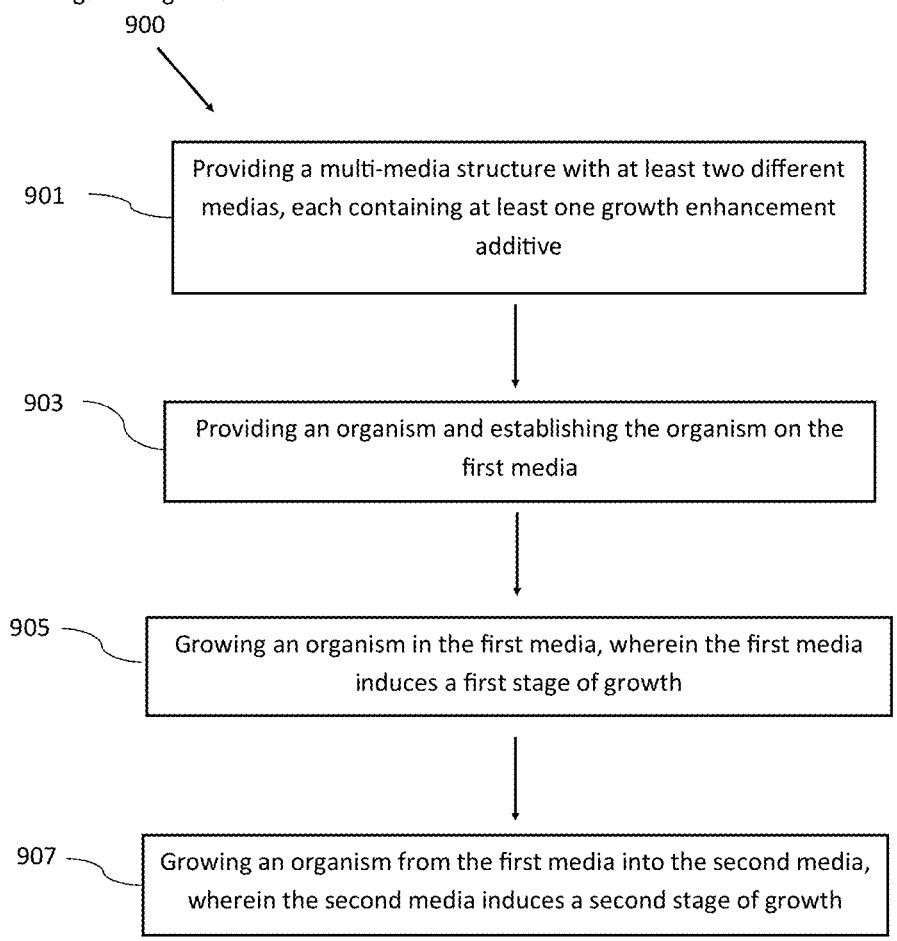
FIG. 9 is a flow diagram for a multi-media structure that supports multiple phases of an organism growth.

FIG. 9 provides a flow diagram showing the use of a multi-media structure to induce different stages of growth in an organism 900, such as a plant. In step 901, a multi-media structure is provided with at least two different medias, each containing at least one growth additive for a specific stage of growth for the plant. For example, in the first media, a root inducing compound or rooting hormone may be incorporated. In step 903, an organism is provided and established on the first media. The organism may comprise for example, a seed, spore, plant tissue culture, hyphae or unrooted cutting. In step 905, an organism is grown on the first media, and the growth enhancement additive induces a first stage of growth. For example, if a rooting hormone has been added to the first media, the first stage of growth is root production of the plant. In step 907, as the organism continues to grow from the first media to the second media, the roots encounter compounds that stimulate a second stage of growth. In this example, the second phase of growth may be vegetative, and the growth enhancement additives in the second media may comprise plant hormones or plant growth regulators that induce vegetative growth in the plant. While not shown in FIG. 9, the multi-media structure may comprise a third media or more media. Here the roots may encounter compounds within the third media that induce a third stage of growth such as flowering, such as gibberellic acid or ethephon.

In the example shown in FIG. 9, two types of media to induce two type so stages of growth are described but any number of media can be used to induce a number of stages of growth in an organism. Therefore, while this descriptive example has types of media, and stages of growth, it should be understood that this description is applicable to other numbers of media and stages of growth, as will be understood by one skilled in the art, once they understand the principles of this invention.

As used herein, the term "stage of growth" includes, but is not limited to, seed germination, seedling, vegetative, bud stage, flowering, ripening, tillering, stem extension, heading, sprout development, tuber initiation, tuber bulking, maturation, main shoot growth, axillary shoot growth, pod development, hyphae elongation (fungi), sclerotia formation (fungi), fungal primodial formational (fungi), diploidization (fungi), spore production (fungi and bacteria), lag phase (bacteria), exponential phase (bacteria), stationary phase (bacteria), and the like.

Embodiments of the present disclosure further provide for production of selective and or differential gas infused gelatinous compounds via the addition of dyes, chemicals, salts, sugars, and antimicrobial agents. Examples of dyes that may be added include, but are not limited to, phenol red, neutral red, congo red, methylene blue, eosin, bromthymol blue, acid fuchsin dyes, iodine, and crystal violet.

Embodiments of the present disclosure further provide for sterilization and disinfection of the gas infused gelatinous compound. The gelatinous solution may be sterilized by moist heat under pressure, such as in an autoclave, or by filtration. Further, the gas infused gelatinous compound may be sterilized after solidification via ionizing radiation. The gelatinous solution may be disinfected by various methods, including but not limited to, heating and pasteurization, the addition of certain chemicals and antimicrobial agents, and by filtration. Further, the gas infused gelatinous compound may be disinfected after solidification via nonionizing radiation.

EXAMPLES

The following examples are provided to illustrate further the various applications and are not intended to limit the invention beyond the limitations set forth in the appended claims.

The gas infused gelatinous compound of the present disclosure may consist of any combination of hydrocolloids and additives, be of various densities, and infused with any type of gas. The following recipes are provided to illustrate further the various compositions and applications and are not intended to limit the invention beyond the limitations set forth in the appended claims.

Example 1—Agar Compounds Infused with Gas

Table 1 below presents examples of gelatinous compounds generated using agar and gas as the gas infused into the gelatinous compound. Solvation was achieved by heating the solution. Aeration was achieved using an apparatus as shown in FIG. 4A and the method of FIG. 5, with a soapstone as the porous material. Column 1 shows the amount of agar used in grams, column 2 shows the amount of water added, column 3 shows the temperature the gelatinous solution was heated to, and column 4 shows the amount of aeration time in minutes. NA=data not available.

TABLE 1

Pectin Compounds Infused With Gas

| Amount of agar | Fill to with water | Temperature heated to | Aeration time |
|---|---|---|---|
| 10 g | 300 ml | 198° F | 20 minutes |
| 10 g | 300 ml | 200° F | 20 minutes |
| 10 g | 300 ml | 208° F | 15 minutes |
| 9 g | 300 ml | 204° F | 20 minutes |
| 8 g | 300 ml | 208° F | 22 minutes |
| 10 g | 300 ml | 165° F | 20 minutes |
| 2.3 g | 100 ml | NA | 26 minutes |
| 5 g | 100 ml | NA | 10 minutes |
| 10 g | 200 ml | NA | 12 minutes |
| 15 g | 300 ml | NA | 20 minutes |
| 8 g | 300 ml | 165° F | 25 minutes |
| 5 g + Miracle-Gro® | 100 ml | NA | 15 minutes |
| 2.3 g | 100 ml | NA | 40 minutes |
| 20 g | 400 ml | 178° F | 22 minutes |
| 12 g | 300 ml | 180° F | 20 minutes |
| 10 g | 300 ml | 180° F | 23 minutes |

Example 2—Pectin Compounds Infused with Gas

Table 2 below presents examples of gas infused gelatinous compounds generated using pectin and gas as the gas infused into the gelatinous compound. Solvation was achieved by heating the solution. Aeration was achieved using an apparatus as shown in FIG. 4A and the method of FIG. 5, with a soapstone as the porous material. Column 1 shows the amount of pectin used in grams plus any additive, column 2 shows the amount of water added, column 3 shows the temperature the gelatinous solution was heated to, and column 4 shows the amount of aeration time in minutes.

TABLE 2

Pectin Compounds Infused With Gas

| Amount of pectin | Fill to with water | Temperature heated to | Aeration time |
|---|---|---|---|
| 8 g | 300 ml | 200° F | 60 minutes |

Example 3—Organisms

The system and methods of the present disclosure may be successfully employed with a wide variety of organisms, including but not limited to wide variety of algae, bacteria, fungi, gymnosperms, angiosperms and pteridophytes, cyanobacteria or eukaryotic green algae. This list of organisms may further include but is not limited to *Arthrospira* spp., *Spirulina* spp., *Calothrix* spp., *Anabaena flos-aquae*, *Aphanizomenon* spp., *Anadaena* spp., *Gleotrichia* spp., *Oscillatoria* spp., *Nostoc* spp., *Synechococcus elongatus*, *Synechococcus* spp., *Synechosystis* spp. PCC 6803, *Synechosystis* spp., *Spirulina plantensis*, *Chaetoceros* spp., *Chlamydomonas reinhardii*, *Chlamydomonas* spp., *Chlorella vulgaris*, *Chlorella* spp., *Cyclotella* spp., *Didymosphenia* spp., *Dunaliella tertiolecta*, *Dunaliella* spp., *Botryococcus braunii*, *Botryococcus* spp., *Gelidium* spp., *Gracilaria* spp., *Hantscia* spp., *Hematococcus* spp., *Isochrysis* spp., *Laminaria* spp., *Navicula* spp., *Pleurochrysis* spp. and *Sargassum* spp; citrus, table grapes, wine grapes, bananas, papaya, *Cannabis* sp., coffee, goji berries, figs, avocados, guava, pineapple, raspberries, blueberries, olives, pistachios, pomegranate, artichokes and almonds; vegetables such as artichokes, asparagus, bean, beets, broccoli, brussel sprouts, chinese cabbage, head cabbage, mustard cabbage, cantaloupe, carrots, cauliflower, celery, chicory, collard greens, cucumbers, daikon, eggplant, endive, garlic, herbs, honey dew melons, kale, lettuce (head, leaf, romaine), mustard greens, okra, onions (dry & green), parsley, peas (sugar, snow, green, black-eyed, crowder, etc.), peppers (bell, chile), pimento, pumpkin, radish, rhubarb, spinach, squash, sweet corn, tomatoes, turnips, turnip greens, watercress, and watermelons; flowering type bedding plants, including, but not limited to, *Ageratum, Alyssum, Begonia, Celosia, Coleus*, dusty miller, *Fuchsia, Gazania*, Geraniums, gerbera daisy, Impatiens, Marigold, *Nicotiana*, pansy/*Viola, Petunia, Portulaca, Salvia*, Snapdragon, Verbena, *Vinca*, and Zinnia; potted flowering plants including, but not limited to, African violet, *Alstroemeria, Anthurium, Azalea, Begonia, Bromeliad, Chrysanthemum, Cineraria, Cyclamen*, Daffodil/Narcissus, *Exacum*, Gardenia, Gloxinia, Hibiscus, Hyacinth, Hydrangea, Kalanchoe, Lily, Orchid, Poinsettia, Primula, regal pelargonium, rose, tulip, *Zygocactus/Schlumbergera*; foliage plants including, but not limited to, *Aglaonema, Anthurium, Bromeliad, Opuntia*, cacti and succulents, Croton, *Dieffenbachia, Dracaena, Epipremnum*, ferns, ficus, *Hedera* (Ivy), *Maranta/Calathea*, palms, *Philodendron, Schefflera, Spathiphyllum*, and *Syngonium*. cut flowers including, but not limited to, *Alstroemeria, Anthurium*, Aster, bird of paradise/Strelitzia, calla lily, carnation, *Chrysanthemum*, Daffodil/Narcissus, daisy, Delphinium, Freesia, gerbera daisy, ginger, Gladiolus, Godetia, Gypsophila, heather, iris, Leptospermum, Liatris, lily, Limonium, Lisianthus, Orchid, Protea, Rose, Statice, Stephanotis, Stock, Sunflower, Tulip; cut cultivated greens including, but not limited to, plumosus, tree fern, boxwood, soniferous greens, Cordyline, Eucalyptus, hedera/Ivy, holly, leatherleaf ferns, Liriope/Lilyturf, Myrtle, Pittosporum, Podocarpus; deciduous shade trees including, but not limited to, ash, birch, honey locust, linden, maple, oak, poplar, sweet gum, and willow; deciduous flowering trees including, but not limited to, Amelanchier, callery pea, crabapple, crapemyrtle, dogwood, flowering cherry, flowering plum, golden rain, hawthorn, Magnolia, and redbud; broadleaf evergreens including, but not limited to, Azalea, cotoneaster, Euonymus, holly, Magnolia, Pieris, Privet, Rhododendron, and Viburnum; coniferous evergreens including, but not limited to, Arborvitae, cedar, cypress, fir, hemlock, juniper, pine, spruce, yew; deciduous shrubs and other ornamentals including, but not limited to, buddleia, hibiscus, lilac, *Spirea, Viburnum, Weigela*, ground cover, bougainvillea, clematis and other climbing vines, and landscape palms; fruit and nut plants including, but not limited to, citrus and subtropical fruit trees, deciduous fruit and nut trees, grapevines, strawberry plants, other small fruit plants, other fruit and nut trees; cut fresh, strawberries, wildflowers, transplants for commercial production, and aquatic plants; pteridophyte plants including, but not limited to ferns and fungi including but not limited to basidiomycetes, ascomycetes, and sacchromycetes. The system of the present disclosure provides a photon pulse for both C3 and C4 photosystems as well as "CAM" plants (Crassulacean acid metabolism).

The multi-media structure as shown in FIGS. 1-3 may be customized for the organism that is intended to grow in it. The following examples outline different arrangements and uses for multi-phase growth of Pteridophytes, Gymnosperms, Angiosperms (monocots and dicots), and Fungi.

Example 4—Multi-Media Structure for the Growth of Fungi

Fungi are a Kingdom of eukaryotic organisms, and thus encompasses a wide diversity of species with varied life cycles and morphologies. Therefore, a wide variety of media types and arrangements may be used to induce vegetative growth and fruiting body production, including but not limited to, agar, enriched sawdust (oak, tan oak, alder, beech, birch, elm, melaleuca, etc), agricultural waste products, rice straw, wheat straw, oat bran, rice bran, wheat bran, sugarcane bagasse, cottonseed hulls, chopped corncobs, etc.

Figure 10:
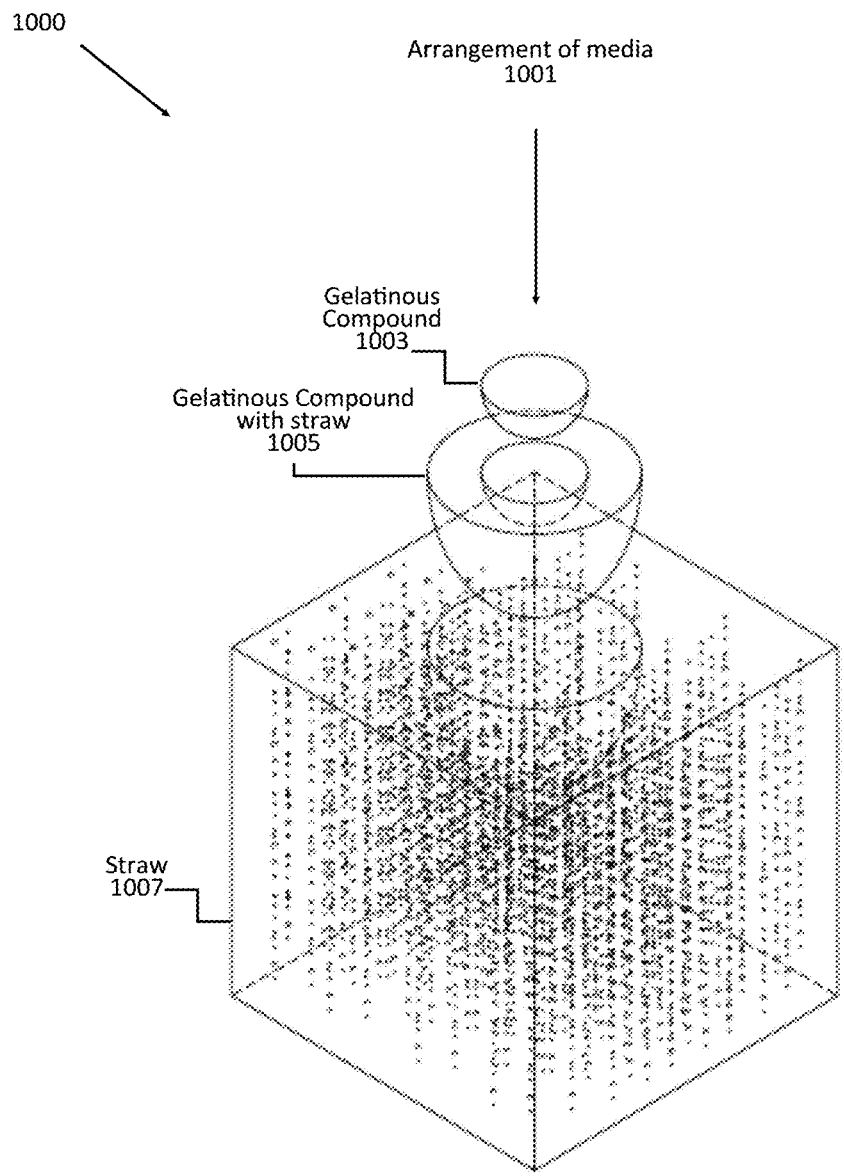
FIG. 10 shows a top perspective view of an example multi-media structure for growing fungi.

FIG. 10 shows an example of a top perspective view of a multi-media structure for growing fungi, such as portabello or cremini mushrooms (*Agaricus bisporus*) or oyster mushrooms (*Pleurotus ostreatus*). In the arrangement of media 1001 of FIG. 10, a first gelatinous compound 1003 is provided, where the first gelatinous compound 1003 (such as malt dexterous agar) contains one or growth enhancement additives. The first gelatinous compound 1003 is formed by taking a gelling agent, such as agar or pectin, which is dissolved in an aqueous solution to produce a liquid gelatinous solution. One or more growth enhancement additives, such as a gas, hormones, nutrients, surfactants, antimicrobial agents, essential oils, herbicides, pesticides, and any combinations thereof may then added to the liquid gelatinous solution. The gelatinous solution is allowed to solidify.

A second gelatinous compound 1005 is provided in FIG. 10, where the second gelatinous compound 1005 contains straw. As with the first gelatinous compound, 1003, the second gelatinous compound 1005 is also formed by taking a gelling agent, such as agar or pectin, which is dissolved in an aqueous solution to produce a liquid gelatinous solution, more or less gelling agents solutions may also be added to increase or decrease the density of the solution. In addition to straw, one or more growth enhancement additives, such as a gas, hormones, nutrients, surfactants, antimicrobial agents, essential oils, herbicides, pesticides, and any combinations thereof may then added to the liquid gelatinous solution. The gelatinous solution is allowed to solidify.

A third media 1007 is provided in FIG. 10, where the media contains straw and may contain one or growth enhancement additives, which may be different from or in different quantities from the additives of the first gelatinous compound 1003 and the second gelatinous compound 1005. The one or more growth enhancement additives, may include, but is not limited to gas, hormones, nutrients, surfactants, antimicrobial agents, essential oils, herbicides, pesticides, and any combinations thereof.

As further shown in FIG. 10, the three media 1003, 1005, and 1007 of the multi-media structure are arranged so that the first gelatinous compound 1003 is embedded into the second gelatinous compound 1005, exposing at least a portion of the surface of the first gelatinous compound 1003 to the environment. The first gelatinous compound 1003 has a shape that substantially corresponds to the shape of the cavity in the second media, gelatinous compound with straw 1005. The gelatinous compound with straw 1005 is embedded into straw 1007, exposing at least a portion of the surface of the second gelatinous compound 1005 to the environment. The second media, gelatinous compound with straw 1005 has a shape that substantially corresponds to the shape of the cavity in the third media, straw 1007.

While a bowl or well-shape cavity is shown in FIG. 10 for the embedding of the different types of media 1003, 1005, and 1007, any shape may be used to fit the media together, including but not limited to, square, rectangle, triangle, oval, trapezium, diamond, rhombus, parallelogram, pentagon, hexagon, heptagon, and octagon.

A variety of sizes may be used for the multi-media structure shown in FIG. 10. For example, the volume of the first type of media may be 0.1% to 99% of the volume of the second type of media. Similarly, the second type of media may be 0.1% to 99% of the volume of the third type of media, and so forth.

While a gelatinous compound, such as agar, and straw is shown as the example in FIG. 10, additional media for growing fungi may include, but is not limited to, compost, peat moss, enriched sawdust (oak, tan oak, alder, beech, birch, elm, melaleuca, etc.), agricultural waste products, rice straw, wheat straw, oat bran, rice bran, wheat bran, sugarcane bagasse, cottonseed hulls, and chopped corncobs In the example shown in FIG. 10, three types of media are illustrated but any number of media can be used. Therefore, while this descriptive example has types of media, 1003, 1005, and 1007, it should be understood that this description is applicable to other numbers of media and gelatinous compounds, as will be understood by one skilled in the art, once they understand the principles of this invention.

The entire multi-media structure 1000 shown in FIG. 10 is designed to support multiple phases of growth of fungi. By way of example, initial vegetative growth of the fungus, such as *Pleurotus ostreatus* may be seen in the first gelatinous compound 1003. Once growth through the first compound 1003, the fungal hyphae may then grow into the second compound 1005, growing into the straw but supported by the gelatinous compound 1005. Finally, the fungi is then able to grow through the second compound 1005 and into the straw 1007, at which point the fungi and the multi-media structure may be induced to produce fruiting bodies. The structure 900 may be planted directly in the ground or in pots or other containers.

Example 5—Multi-Media Structure for the Growth of Pteridophytes

Pteridophytes are vascular plants that reproduce via spores, and include ferns, horsetails, clubmosses, spikemosses, and quillworts. A top perspective view of an example multi-media structure of the present disclosure for the growth of ferns is shown in FIG. 11.

Figure 11:
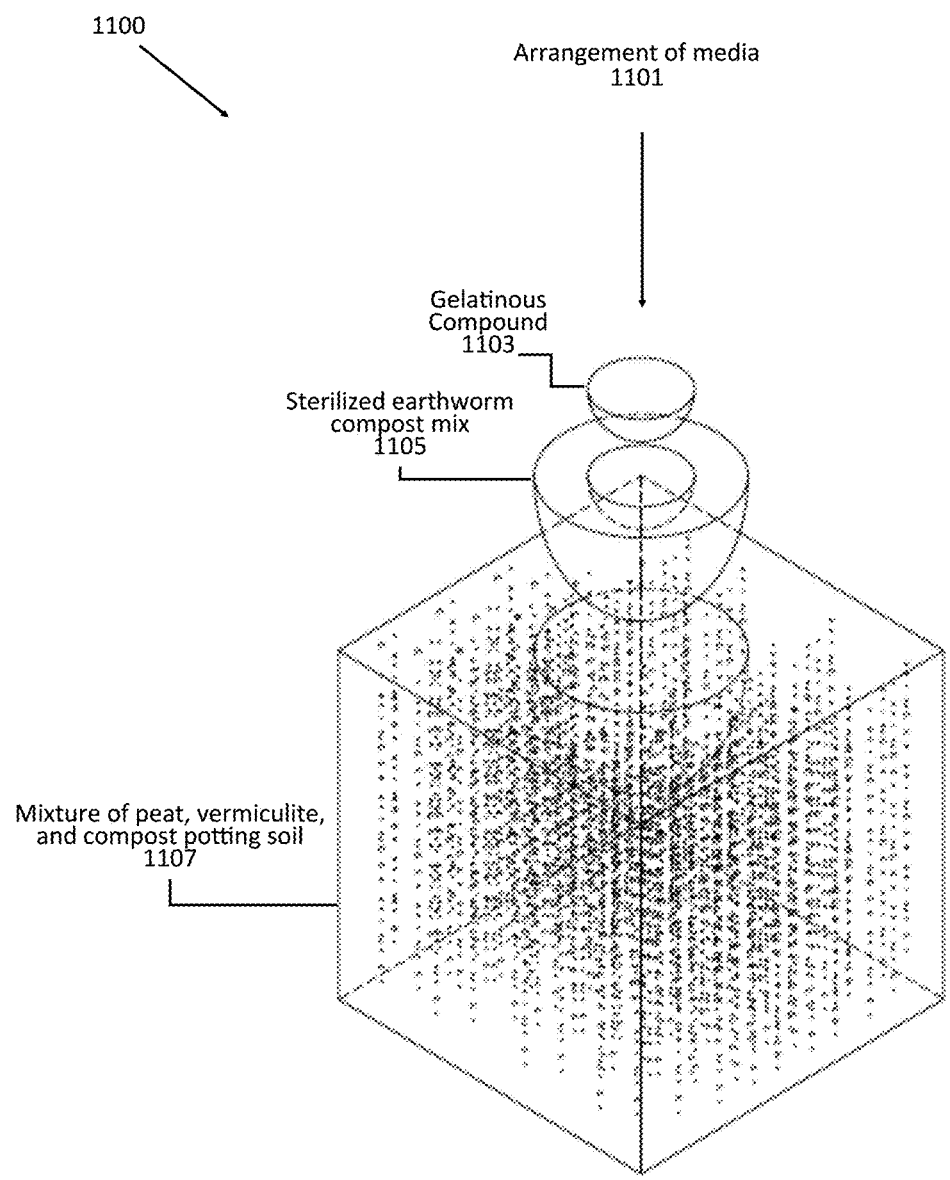
FIG. 11 shows a top perspective view of an example multi-media structure for growing ferns.

In the arrangement of media 1101 of FIG. 11, a first gelatinous compound 1103 is provided, where the first gelatinous compound 1103 contains one or growth enhancement additives. The first gelatinous compound 1103 is formed by taking a gelling agent, such as agar or pectin, which is dissolved in an aqueous solution to produce a liquid gelatinous solution. One or more growth enhancement additives, such as a gas, hormones, nutrients, surfactants, antimicrobial agents, essential oils, herbicides, pesticides, and any combinations thereof may then added to the liquid gelatinous solution. The gelatinous solution is allowed to solidify.

A second media 1105 is provided in FIG. 11, where by example the second media 1105 is sterilized earthworm compost mix 1105. In addition to the compost mix, one or more growth enhancement additives, such as a gas, hormones, nutrients, surfactants, antimicrobial agents, essential oils, herbicides, pesticides, and any combinations thereof may then be added.

A third media 1107 is provided in FIG. 11, where by example the media contains a mixture of peat, vermiculite, and compost potting soil 1107 and may contain one or growth enhancement additives, which may be different from or in different quantities from the additives of the first gelatinous compound 1103 and the second media 1105. The one or more growth enhancement additives, may include, but is not limited to gas, hormones, nutrients, surfactants, antimicrobial agents, essential oils, herbicides, pesticides, and any combinations thereof.

As further shown in FIG. 11, the three media 1103, 1105, and 1107 of the multi-media structure are arranged so that the first gelatinous compound 1103 is embedded into the second media 1105, exposing at least a portion of the surface of the first gelatinous compound 1103 to the environment. The first gelatinous compound 1103 has a shape that substantially corresponds to the shape of the cavity in the second media, 1105. The second media 1105 is embedded into the third media 1107, exposing at least a portion of the surface of the second media 1105 to the environment. The second media 1105 has a shape that substantially corresponds to the shape of the cavity in the third media 1107.

While a bowl or well-shape cavity is shown in FIG. 11 for the embedding of the different types of media 1103, 1105, and 1107, any shape may be used to fit the media together, including but not limited to, square, rectangle, triangle, oval, trapezium, diamond, rhombus, parallelogram, pentagon, hexagon, heptagon, and octagon.

A variety of sizes may be used for the multi-media structure shown in FIG. 11. For example, the volume of the first type of media may be 0.1% to 99% of the volume of the second type of media. Similarly, the second type of media may be 0.1% to 99% of the volume of the third type of media, and so forth.

While the example gelatinous compound 1103, earthworm compost mix 1105, and a mixture of peat, vermiculite, and compost potting soil 1107 are shown as the example in FIG. 11, additional media and different arrangements of media may be used for growing pteridophytes such as ferns.

Additionally, while the example shown in FIG. 11 has three types of media, any number of media can be used. Therefore, while this descriptive example has types of media, 1103, 1105, and 1107, it should be understood that this description is applicable to other numbers of media and gelatinous compounds, as will be understood by one skilled in the art, once they understand the principles of this invention.

The entire multi-media structure 1100 shown in FIG. 11 is designed to support multiple phases of growth of a fern plant. By way of example, initial spore germination and root development may be seen in the first gelatinous compound 1103. Once growth through the first compound 1103, the fern roots may then grow into the earthworm compost mix 1105. Finally, the roots of the fern are then able to grow through the second compound 1105 and into the mixture of peat, vermiculite, and compost potting soil 1107. The structure 1100 may be planted directly in the ground or in pots or hanging baskets.

Example 6—Multi-Media Structure for the Growth of Gymnosperms

Gymnosperms are a group of plants that bear seed in a cone. An example of a gymnosperm includes gingko, ephedra and conifers, which includes cedars, Douglas-fir, cypresses, fir, junipers, kauri, larch, pines, hemlocks, redwoods, spruces, and yews. A top perspective view of an example use of the multi-media structure of the present disclosure for growing conifers is shown in FIG. 12.

Figure 12:
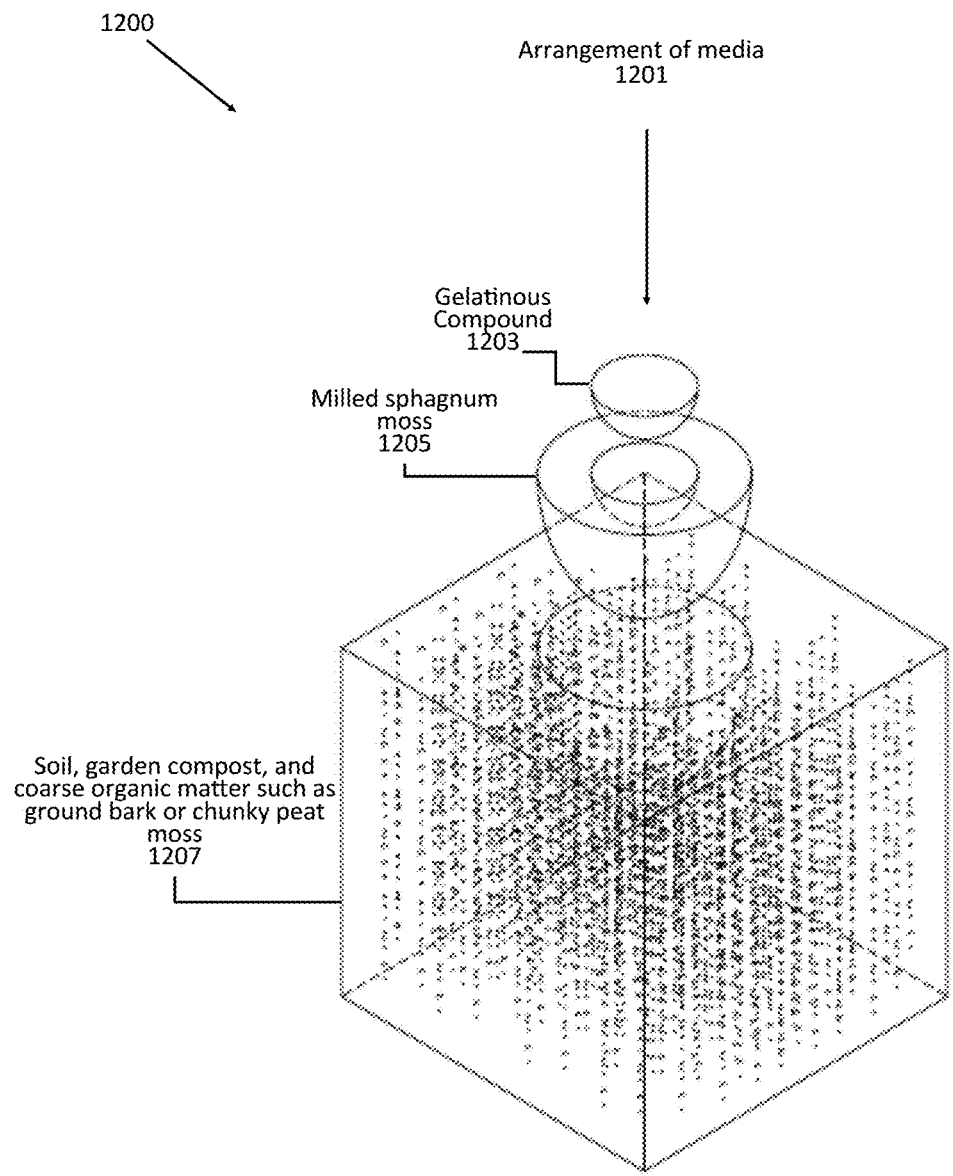
FIG. 12 shows a top perspective view of an example multi-media structure for growing conifers.

In the arrangement of media 1201 of FIG. 12, a first gelatinous compound 1203 is provided, where the first gelatinous compound 1203 contains one or growth enhancement additives. The first gelatinous compound 1203 is formed by taking a gelling agent, such as agar or pectin, which is dissolved in an aqueous solution to produce a liquid gelatinous solution. One or more growth enhancement additives, such as a gas, hormones, nutrients, surfactants, antimicrobial agents, essential oils, herbicides, pesticides, and any combinations thereof may then added to the liquid gelatinous solution. The gelatinous solution is allowed to solidify.

A second media 1205 is provided in FIG. 12, where by example second media 1205 is milled sphagnum moss 1205. In addition to the milled sphagnum moss, one or more growth enhancement additives, such as a gas, hormones, nutrients, surfactants, antimicrobial agents, essential oils, herbicides, pesticides, and any combinations thereof may then added.

A third media 1207 is provided in FIG. 12, where by example media contains a mixture of soil, garden compost, and coarse organic matter such as ground bark or chunky peat moss 1207 and may contain one or growth enhancement additives, which may be different from or in different quantities from the additives of the first gelatinous compound 1203 and the second media 1205. The one or more growth enhancement additives, may include, but are not limited to gas, hormones, nutrients, surfactants, antimicrobial agents, essential oils, herbicides, pesticides, and any combinations thereof.

As further shown in FIG. 12, the three media 1203, 1205, and 1207 of the multi-media structure are arranged so that the first gelatinous compound 1203 is embedded into the second media 1205, exposing at least a portion of the surface of the first gelatinous compound 1203 to the environment. The first gelatinous compound 1203 has a shape that substantially corresponds to the shape of the well in the second media, 1205. The second media 1205 is embedded into the third media 1207, exposing at least a portion of the surface of the second media 1205 to the environment. The second media 1205 has a shape that substantially corresponds to the shape of the well in the third media 1207.

While a bowl or well-shape is shown in FIG. 12 for the embedding of the different types of media 1203, 1205, and 1207, any shape may be used to fit the media together, including but not limited to, square, rectangle, triangle, oval, trapezium, diamond, rhombus, parallelogram, pentagon, hexagon, heptagon, and octagon.

A variety of sizes may be used for the multi-media structure shown in FIG. 12. For example, the volume of the first type of media may be 0.1% to 99% of the volume of the second type of media. Similarly, the second type of media may be 0.1% to 99% of the volume of the third type of media, and so forth.

While a gelatinous compound 1203, milled sphagnum moss 1205, and a mixture of soil, garden compost, and coarse organic matter such as ground bark or chunky peat moss 1207 are shown as the example in FIG. 12, additional media and different arrangements of media may be used for growing gymnosperms such as conifers, including but not limited to, damp peat moss, vermiculite, and perlite.

Additionally, while the example shown in FIG. 12 has three types of media, any number of media can be used. Therefore, while this descriptive example has types of media, 1203, 1205, and 1207, it should be understood that this description is applicable to other numbers of media and gelatinous compounds, as will be understood by one skilled in the art, once they understand the principles of this invention.

The entire multi-media structure 1200 shown in FIG. 12 is designed to support multiple phases of growth of a conifer plant. By way of example, initial seed germination and root development may be seen in the first gelatinous compound 1203. Once growth through the first compound 1203, the conifer roots may then grow into the milled sphagnum moss 1205. Finally, the roots of the conifer is then able to grow through the second compound 1205 and into the mixture of soil, garden compost, and coarse organic matter such as ground bark or chunky peat moss 1207. The structure 1200 may be planted directly in the ground or in pots or hanging baskets.

Example 7—Multi-Media Structure for the Growth of Legumes (An Angiosperm)

Angiosperms are seed-bearing flowering vascular plants, and include monocots and dicots. While there are an estimated 352,000 species of flowering plants spanning trees, herbs, submerged aquatics, bulbs, and epiphytes, the largest families are orchids, Compositae (daisies), and legumes. A top perspective view of an example multi-media structure for growing legumes is shown in FIG. 13.

Figure 13:
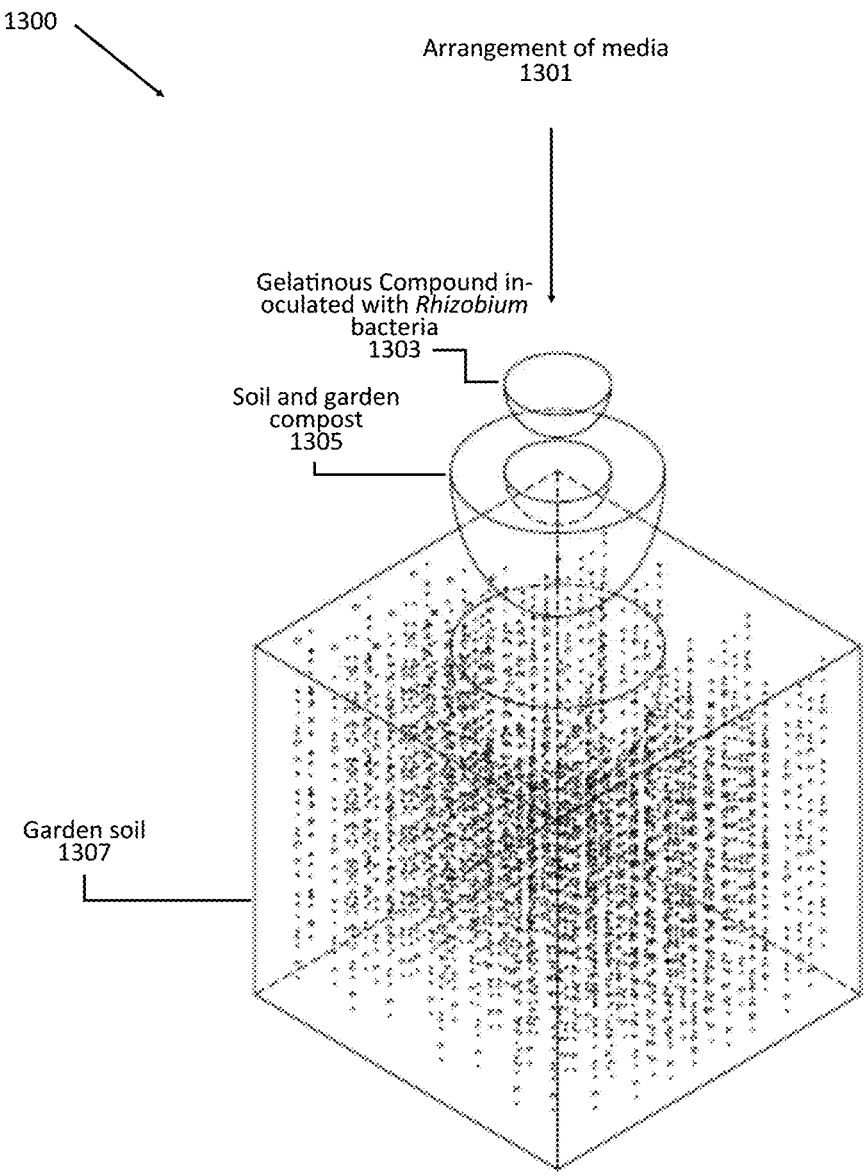
FIG. 13 shows a top perspective view of an example multi-media structure for growing legumes.

In the arrangement of media 1301 of FIG. 13, a first gelatinous compound 1303 is provided, where the first gelatinous compound 1303 contains an inoculant of *Rhizobium* bacteria strains, as these strains of bacteria have a symbiotic relationship with legumes, such as soybeans. The first gelatinous compound 1303 may additionally contain one or growth enhancement additives. The first gelatinous compound 1303 is formed by taking a gelling agent, such as agar or pectin, which is dissolved in an aqueous solution to produce a liquid gelatinous solution. One or more growth enhancement additives, such as a gas, hormones, nutrients, surfactants, antimicrobial agents, essential oils, herbicides, pesticides, and any combinations thereof may then be added to the liquid gelatinous solution. The gelatinous solution is allowed to solidify. The inoculation of *Rhizobium* bacteria may occur prior to solidification, as in the pour plate method, or after, via the spread or streak plate method, or may be a stab culture.

A second media 1305 is provided in FIG. 13, where the second media 1305 is soil mixed with garden compost 1305. In addition to the soil mixed with garden compost, one or more growth enhancement additives, such as a gas, hormones, nutrients, surfactants, antimicrobial agents, essential oils, herbicides, pesticides, and any combinations thereof may then added.

A third media 1307 is provided in FIG. 13, where the media is garden soil 1307 and may contain one or more growth enhancement additives, which may be different from or in different quantities from the additives of the first gelatinous compound 1303 and the second media 1305. The one or more growth enhancement additives, may include, but are not limited to gas, hormones, nutrients, surfactants, antimicrobial agents, essential oils, herbicides, pesticides, and any combinations thereof.

As further shown in FIG. 13, the three media 1303, 1305, and 1307 of the multi-media structure are arranged so that the first gelatinous compound 1303 is embedded into the second media 1305, exposing at least a portion of the surface of the first gelatinous compound 1303 to the environment. The first gelatinous compound 1303 has a shape that substantially corresponds to the shape of the cavity in the second media, 1305. The second media 1305 is embedded into the third media 1307, exposing at least a portion of the surface of the second media 1305 to the environment. The second media 1305 has a shape that substantially corresponds to the shape of the cavity in the third media 1307.

While a bowl or well-shape cavity is shown in FIG. 13 for the embedding of the different types of media 1303, 1305, and 1307, any shape may be used to fit the media together, including but not limited to, square, rectangle, triangle, oval, trapezium, diamond, rhombus, parallelogram, pentagon, hexagon, heptagon, and octagon.

A variety of sizes may be used for the multi-media structure shown in FIG. 13. For example, the volume of the first type of media may be 0.1% to 99% of the volume of the second type of media. Similarly, the second type of media may be 0.1% to 99% of the volume of the third type of media, and so forth.

While a gelatinous compound inoculated with *Rhizobium* bacteria 1303, soil mixed with garden compost 1305, and garden soil 1307 are shown as the example in FIG. 13, additional media and different arrangements of media may be used for growing legumes.

Additionally, while the example shown in FIG. 13 has three types of media, any number of media can be used. Therefore, while this descriptive example has types of media, 1303, 1305, and 1307, it should be understood that this description is applicable to other numbers of media and gelatinous compounds, as will be understood by one skilled in the art, once they understand the principles of this invention.

The entire multi-media structure 1300 shown in FIG. 13 is designed to support multiple phases of growth of a legume plant. By way of example, initial seed germination and root development may be seen in the first gelatinous compound 1303. Once growth through the first compound 1303, the legume roots may then grow into the soil mixed with garden compost 1305. Finally, the roots of the conifer is then able to grow through the second compound 1305 and into the garden soil 1307. The structure 1300 may be planted directly in the ground or in pots or hanging baskets.

Example 8—Multi-Media Structure for the Growth of Orchids (An Angiosperm)

The multi-media structure of the present disclosure may be used to grow orchids. Orchid seeds can be difficult to grow since they require a mycorrhizal fungus. Thus, while not shown in a figure, an example use of the multi-media structure of the present disclosure to grow orchids may consist of a first media comprised of the potting media of the parent plant, which would contain the mycorrhizal fungus required by the orchid seed for the necessary nutrients to grow. Alternatively, another common method for starting orchid seeds is a nutrient solution mixed with agar, and thus this may also be used as the first media.

With either first media, the second type of media may be composed of sphagnum moss and peat moss. The first and or second media may include specific nutrients tailored to orchids. As with the examples described above, the multi-media structure is arranged so that the first media is embedded into the second media, exposing at least a portion of the surface of the first media to the environment. The first media would have a shape that substantially corresponds to the shape created in the second media. Any shape may be used to fit the media together, including but not limited to, well or bowl shaped cavity, square, rectangle, triangle, oval, trapezium, diamond, rhombus, parallelogram, pentagon, hexagon, heptagon, and octagon.

A variety of sizes may be used for the multi-media structure described for growing orchids. For example, the volume of the first type of media may be 0.1% to 99% of the volume of the second type of media, and so forth. Additional media and different arrangements of media may be used for growing orchids. Thus, while the example described above has two types of media, any number of media can be used, as will be understood by one skilled in the art, once they understand the principles of this invention.

The entire multi-media structure described above for the growth of orchids is designed to support multiple phases of growth. By way of example, root development may be seen in the first compound of the multi-media structure. Once growth through the first compound, the orchid roots may then grow into the second compound. Finally, the roots of the orchid are then able to grow through the second compound and into the third compound. The structure may be planted directly into pots or hanging baskets.

Example 9—Multi-Media Structure for the Growth of Daises (An Angiosperm)

The multi-media structure of the present disclosure may be used to grow daisies. While not shown in a figure, an example use of the multi-media structure of the present disclosure to grow daisies may consist of a first media comprised of a gelatinous compound with growth enhancement additives tailored to daises. The first gelatinous compound may be formed by taking a gelling agent, such as agar or pectin, which is dissolved in an aqueous solution to produce a liquid gelatinous solution. One or more growth enhancement additives, such as a gas, hormones, nutrients, surfactants, antimicrobial agents, essential oils, herbicides, pesticides, and any combinations thereof may then added to the liquid gelatinous solution.

The second type of media for the growth of daisies may be composed of potting soil. The second media may have growth enhancement additives that are different from, or in different quantities than those included in the first media. As with the examples described above, the multi-media structure is arranged so that the first media is embedded into the second media, exposing at least a portion of the surface of the first media to the environment. The first media would have a shape that substantially corresponds to the shape created in the second media. Any shape may be used to fit the media together, including but not limited to, well or bowl shaped, square, rectangle, triangle, oval, trapezium, diamond, rhombus, parallelogram, pentagon, hexagon, heptagon, and octagon.

A variety of sizes may be used for the multi-media structure described for growing daises. For example, the volume of the first type of media may be 0.1% to 99% of the volume of the second type of media, and so forth. Additional media and different arrangements of media may be used for growing daisies. Thus, while the example described above has two types of media, any number of media can be used, as will be understood by one skilled in the art, once they understand the principles of this invention.

The entire multi-media structure described above for the growth of daisies is designed to support multiple phases of growth. The structure may be planted directly in the ground or into pots or hanging baskets.

Example 10—Using Liquid as Media 1 or 2

In another example of the present disclosure, the multi-media structure may include a layer of liquid media, as the first compound or the second compound. In this example liquid media, containing various types of nutrients may be provided to promote initial plant or organism growth.

For the use of a liquid media as the first media, the second type of media provided may be a gelatinous compound or a solid substrate, containing one or more growth enhancement additives, including, but not limited to gas, hormones, nutrients, surfactants, antimicrobial agents, essential oils, herbicides, pesticides, and any combinations thereof. A cavity is formed in the surface of the second compound, creating a reservoir for the liquid media of the first layer. The second media may have growth enhancement additives that are different from, or in different quantities than those included in the first media.

A third media may then be provided where the second media is imbedded in the third media. As described above, the third compound maybe a gelatinous compound or a solid substrate containing one or growth enhancement additives, which may be different from or in different quantities from the additives of the first liquid media and the second media.

In this example, the multi-media structure may be placed on a shaker to allow for agitation and aeration of the liquid media. As the organism in the liquid media develops, roots or hyphae extend from the organism through the liquid media and attached to the second media compound. As the nutrients of the liquid media are exhausted, the organism grows into the second layer. At this point, the liquid media may be poured off or the media may be agitated to allow for aeration, depending on the specific needs of the organism.

In another example, the first compound of the multi-media structure is a gelatinous compound that floats on a second layer of liquid media, where the liquid media is contained in a reservoir a third, base substrate or compound.

The foregoing description has been presented for purposes of illustration and description. It is not intended to be exhaustive or to limit to the precise form disclosed. While a number of exemplary aspects and embodiments have been discussed above, those of skill in the art will recognize certain modifications, permutations, additions and sub-combinations thereof. The embodiments were chosen and described in order to best explain the principles and its practical application to thereby enable others skilled in the art to best utilize in various embodiments and various modifications as are suited to the particular use contemplated. It is therefore intended that the following appended claims and claims hereafter introduced are interpreted to include all such modifications, permutations, additions, and sub-combinations as are within their true spirit and scope.

What is claimed is:

1. A multi-media gelatinous structure for the growth of an organism, wherein said structure comprises:
   a first gelatinous compound, wherein said first gelatinous compound is infused with a gas and comprises at least one growth enhancement additive selected from hormones, essential oils, antimicrobial agents, herbicides, pesticides, and microbes;
   a second gelatinous compound, wherein said second gelatinous compound is infused with a gas and comprises at least one growth enhancement additive selected from hormones, essential oils, antimicrobial agents, herbicides, pesticides, and microbes, and wherein the at least one growth enhancement additive of the second gelatinous compound is different from or in a different quantity from the at least one growth enhancement additive of the first gelatinous compound;
   wherein said first gelatinous compound and said second gelatinous compound are produced by a combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch;

wherein the density of said gelatinous compound of said first gelatinous compound is greater than the density of said gelatinous compound of said second gelatinous compound; and wherein said first gelatinous compound is embedded within said second gelatinous compound to create a multi-media gelatinous structure.

2. The multi-media gelatinous structure of claim 1, wherein said structure further comprises:

a third gelatinous compound, wherein said third gelatinous compound is infused with a gas and comprises at least one growth enhancement additive selected from hormones, essential oils, antimicrobial agents, herbicides, pesticides, and microbes, and wherein the at least one growth enhancement additive of the third gelatinous compound is different from or in a different quantity from the at least one growth enhancement additive of the first gelatinous compound and the second gelatinous compound, wherein said third gelatinous compound is produced by a combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch;

wherein the density of said gelatinous compound of said third gelatinous compound is less than the density of said first gelatinous compound and said second gelatinous compound; and wherein said first gelatinous compound and said second gelatinous compound are embedded within said third gelatinous compound.

3. The multi-media structure of claim 1, wherein said gas is produced by aerating said gelatinous compounds when said gelatinous compounds are a gelatinous solution to produce bubbles and infuse the gelatinous solution with a gas.

4. The multi-media structure of claim 3, wherein said gas is produced by aerating said gelatinous compounds, wherein said aeration is produced by a chemical process.

5. The multi-media structure of claim 1, wherein said first gelatinous compound or said second gelatinous compound further comprise a dye.

6. The multi-media structure of claim 2, wherein said third gelatinous compound further comprises a dye.

7. A method for growing plants in a multi-media gelatinous structure, wherein said method comprises:

dissolving a gelling agent, wherein said gelling agent consists of any one or any combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch, and one or more growth enhancement additives into a first aqueous solution, wherein said one or more growth enhancement additives are selected from hormones, essential oils, antimicrobial agents, herbicides, pesticides, and microbes;

dissolving a gelling agent, wherein said gelling agent consists of any one or any combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch, and one or more growth enhancement additives into at least one second aqueous solution, wherein said one or more growth enhancement additives are selected from hormones, essential oils, antimicrobial agents, herbicides, pesticides, and microbes;

pouring said first aqueous solution and said at least one second aqueous solution into separate containers;

allowing said first aqueous solution and said at least one second aqueous solution to solidify to produce a first gelatinous compound and a second gelatinous compound, wherein the density of said first gelatinous compound is greater than the density of said second gelatinous compound;

releasing said gelatinous compounds from said containers;

embedding said first gelatinous compound within said second gelatinous compound to create a stacked gelatinous media;

placing a plant on the surface of said first gelatinous compound of said stacked gelatinous media; and growing said plant in said stacked gelatinous media.

8. The method of claim 7 further comprising aerating at least one of said first gelatinous compound and said second gelatinous compound to produce bubbles and infuse at least one of the gelatinous solutions with a gas.

9. The method of claim 8, further comprising adding an additional one or more growth enhancement additives prior to aeration.

10. The method of claim 7, further comprising adding one or more growth enhancement additives to the surface of said first gelatinous and said second gelatinous compound after solidification and prior to stacking.

11. The method of claim 7, wherein said dissolving is achieved by heating the gelling agent and aqueous solutions.

12. The method of claim 7, further comprising adding a surfactant to said first aqueous solution or said second aqueous solution.

13. The method of claim 7, further comprising adding a dye to at least one of said first gelatinous compound and said second gelatinous compound.

14. The method of claim 8, wherein said aeration of the gelatinous solutions is achieved by a chemical reaction.

15. The method of claim 7, wherein said gas is selected from the group consisting of oxygen, carbon dioxide, ethylene, nitrogen, argon, methane, helium, and combinations thereof.

16. The method of claim 7, further comprising the disinfection or sterilization of said gelatinous compounds.

17. A method for growing an organism through multiple stages of growth, the method comprising:

providing a multi-media structure comprising at least a first gelatinous compound and a second gelatinous compound, wherein the first gelatinous compound comprises at least one growth enhancement additive selected from hormones, essential oils, antimicrobial agents, herbicides, pesticides, and microbes; and wherein said second gelatinous compound comprises at least one growth enhancement additive selected from hormones, essential oils, antimicrobial agents, herbicides, pesticides, and microbes; and wherein the at least one growth enhancement additive of the second gelatinous compound is different from or in a different quantity from the at least one growth enhancement additive of the first gelatinous compound;

and wherein said first gelatinous compound and said second gelatinous compound are produced by a combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch, wherein the density of said gelatinous compound of said first gelatinous compound is greater than the density of said gelatinous compound of said second gelatinous compound;

providing an organism and establishing said organism on the surface of said first gelatinous compound, wherein said organism is established on said first gelatinous compound;

growing said organism on said first gelatinous compound;

allowing said organism to grow through said first gelatinous compound and into said second gelatinous compound.

18. The method of claim 17, further comprising:

providing a third gelatinous compound, wherein said third gelatinous compound comprises at least one growth enhancement additive selected from hormones, essential oils, antimicrobial agents, herbicides, pesticides, and microbes, and wherein the at least one growth enhancement additive of the third gelatinous compound is different from or in a different quantity from the growth enhancement additive of the first gelatinous compound and the growth enhancement additive of the second gelatinous compound;

wherein said third gelatinous compound is produced by a combination of hydrocolloids, wherein said hydrocolloids are selected from the group consisting of pectin, gelatin, agar-agar, xanthan gum, guar gum, locust bean gum, gum arabic, carrageenan, cellulose and cellulose derivatives such as carboxymethyl cellulose, alginate, and starch, wherein the density of said gelatinous compound of said third gelatinous compound is less than the density of said first gelatinous compound and said second gelatinous compound; and allowing said organism to grow from said second gelatinous compound and into said third gelatinous compound.

19. The method of claim 17, wherein said organism is selected from a microorganism, bacteria, fungi, and plant.

20. The method of claim 17, wherein said organism is established on said first gelatinous compound in a first growth stage.

21. The method of claim 20, wherein said organism is allowed to grow through said first gelatinous compound, into said second gelatinous compound.

22. The method of claim 21, wherein when said organism reaches said second gelatinous compound, said second gelatinous compound induces said organism to move from said first growth stage and into a second growth stage.

23. The method of claim 22, wherein said first stage of growth and said second stage of growth are selected from seed germination, seedling, vegetative, bud stage, flowering, ripening, tillering, stem extension, heading, sprout development, tuber initiation, tuber bulking, maturation, main shoot growth, axillary shoot growth, pod development, hyphae elongation, diploidization, spore production, lag phase, exponential phase, and stationary phase.

\* \* \* \* \*